United States Patent [19]
Engelson et al.

[11] Patent Number: 5,972,019
[45] Date of Patent: Oct. 26, 1999

[54] MECHANICAL CLOT TREATMENT DEVICE

[75] Inventors: Erik T. Engelson, Menlo Park; Gene Samson, Milpitas; Kim Nguyen, San Jose; Rose Y. Wong, San Francisco, all of Calif.

[73] Assignee: Target Therapeutics, Inc., Fremont, Calif.

[21] Appl. No.: 08/869,346

[22] Filed: Jun. 5, 1997

Related U.S. Application Data

[63] Continuation-in-part of application No. 08/686,304, Jul. 25, 1996, and application No. 08/701,155, Aug. 21, 1996, abandoned.

[51] Int. Cl.$^6$ .................................................. A61M 29/00
[52] U.S. Cl. ............................................ 606/200; 606/159
[58] Field of Search .................................... 606/200, 180, 606/170, 159; 604/107, 108, 104, 105, 106

[56] References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,367,101 | 2/1968 | Garner et al. . |
| 3,435,826 | 4/1969 | Fogarty . |
| 3,753,700 | 8/1973 | Harrison et al. . |
| 3,996,938 | 12/1976 | Clark, III . |
| 4,030,503 | 6/1977 | Clark, III . |
| 4,403,612 | 9/1983 | Fogarty . |
| 4,706,671 | 11/1987 | Weinrib . |
| 4,762,130 | 8/1988 | Fogarty et al. . |
| 4,885,003 | 12/1989 | Hillstead . |
| 4,890,611 | 1/1990 | Monfort et al. . |
| 4,904,431 | 2/1990 | O'Maleki . |
| 4,921,484 | 5/1990 | Hillstead . |
| 5,011,488 | 4/1991 | Ginsburg . |
| 5,112,347 | 5/1992 | Taheri . |
| 5,122,136 | 6/1992 | Guglielmi et al. . |
| 5,133,733 | 7/1992 | Rasmussen et al. . |
| 5,192,286 | 3/1993 | Phan et al. . |
| 5,308,354 | 5/1994 | Zacca et al. ......................... 606/159 |
| 5,330,484 | 7/1994 | Gunther et al. . |
| 5,354,295 | 10/1994 | Guglielmi et al. . |
| 5,411,509 | 5/1995 | Hilal . |
| 5,423,829 | 6/1995 | Pham et al. . |
| 5,449,372 | 9/1995 | Schmaltz et al. . |
| 5,454,795 | 10/1995 | Samson . |
| 5,456,667 | 10/1995 | Ham et al. . |
| 5,490,859 | 2/1996 | Mische et al. . |
| 5,527,326 | 6/1996 | Hermann et al. . |
| 5,643,297 | 7/1997 | Nordgren et al. . |
| 5,643,298 | 7/1997 | Nordgren et al. . |
| 5,695,469 | 12/1997 | Segal . |
| 5,792,157 | 8/1998 | Mische et al. . |
| 5,843,103 | 12/1998 | Wulfman . |

FOREIGN PATENT DOCUMENTS

| | | |
|---|---|---|
| 2000621 | 4/1990 | Canada . |
| 0117940 | 9/1984 | European Pat. Off. . |
| 0418677 | 3/1991 | European Pat. Off. . |
| 0472368 | 2/1992 | European Pat. Off. . |
| 0531822 | 3/1993 | European Pat. Off. . |
| 0533511 | 3/1993 | European Pat. Off. . |
| 0737450 | 10/1996 | European Pat. Off. . |
| 94/24946 | 11/1994 | WIPO . |
| WO 95/35066 | 12/1995 | WIPO . |
| 96/01591 | 1/1996 | WIPO . |
| WO 97/42878 | 11/1997 | WIPO . |

OTHER PUBLICATIONS

Catañeda–Zúñiga, ed., *Interventional Radiology*, vol. 1, Third Edition, Williams & Wilkins, New York, 1997, pp. 912–921.

*Primary Examiner*—Michael Buiz
*Assistant Examiner*—Julian W. Woo
*Attorney, Agent, or Firm*—Morrison & Foerster LLP

[57] ABSTRACT

This is a medical device. In particular, it is a surgical device usually delivered through an intravascular catheter. It may be used in several ways. It may, for instance, be used to open a clear passageway adjacent thrombus to allow both blood and medication to bypass the clot. It may be used to pierce and to remove thrombus. These thrombus are often found in tortuous vasculature. The device includes several sections. The device has a core element, typically a core wire. Placed around the distal end of the core element is a collapsible but preferably self expanding cage assembly. The cage assembly is preferably radio-opaque. The proximal end of the cage is typically is affixed to an actuator in such a way as to allow expansion of the cage after deployment. The cage assembly may have a generally conical distal or "trailing" portion when expanded and also a proximal section. The cage assembly may be used for collecting emboli or for displacing them to allow blood flow to resume. The proximal section may have various uses, e.g., for centering the collector assembly in the vascular lumen or for gathering larger amounts of the targeted clot or to act as a passageway for fluid flow. The assembly further may have an actuator which permits or causes the collector assembly to expand after deployment.

35 Claims, 20 Drawing Sheets

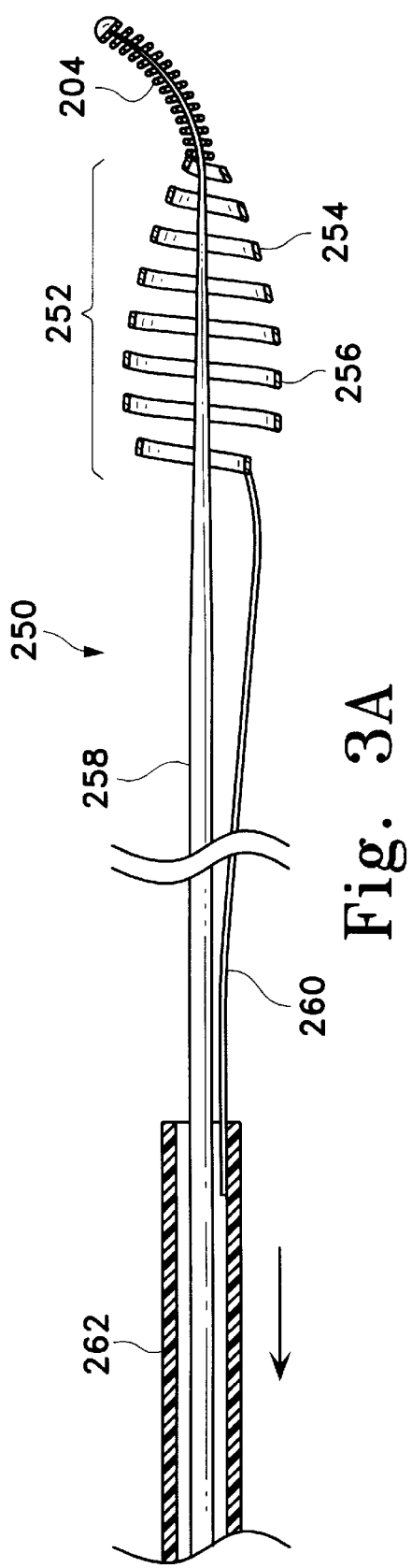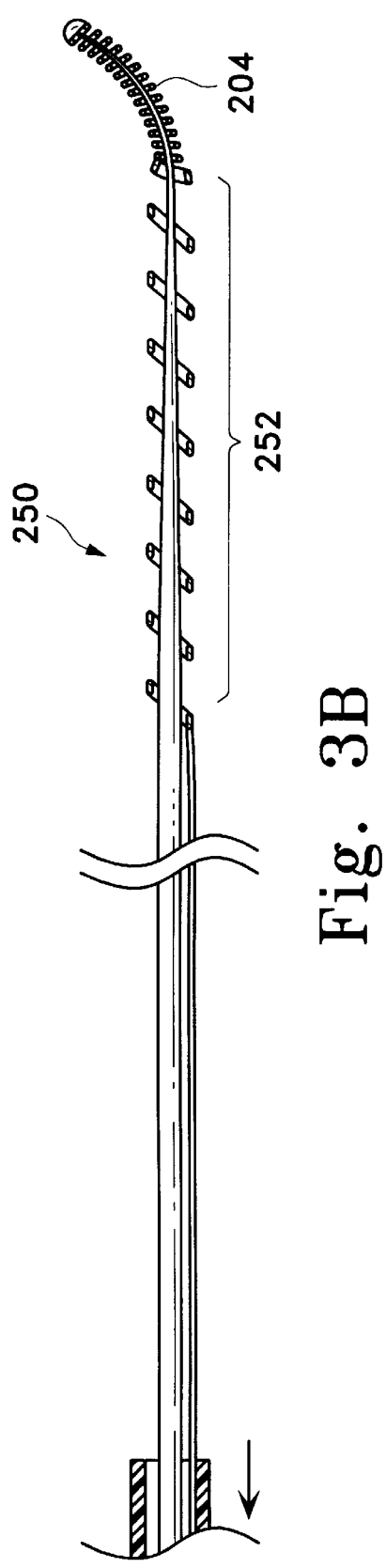
Fig. 3A
Fig. 3B

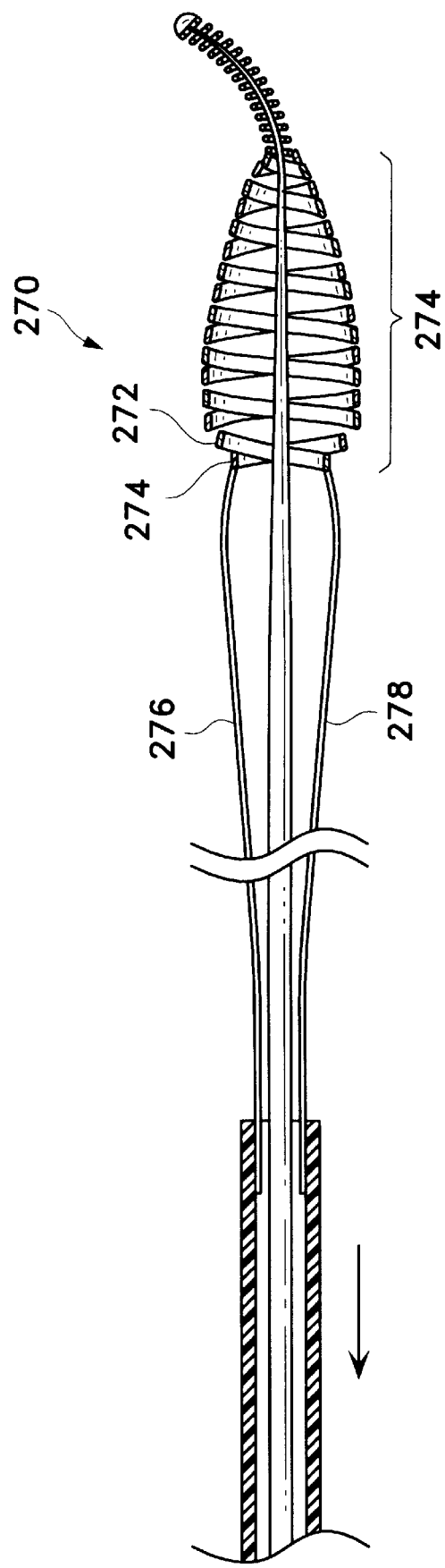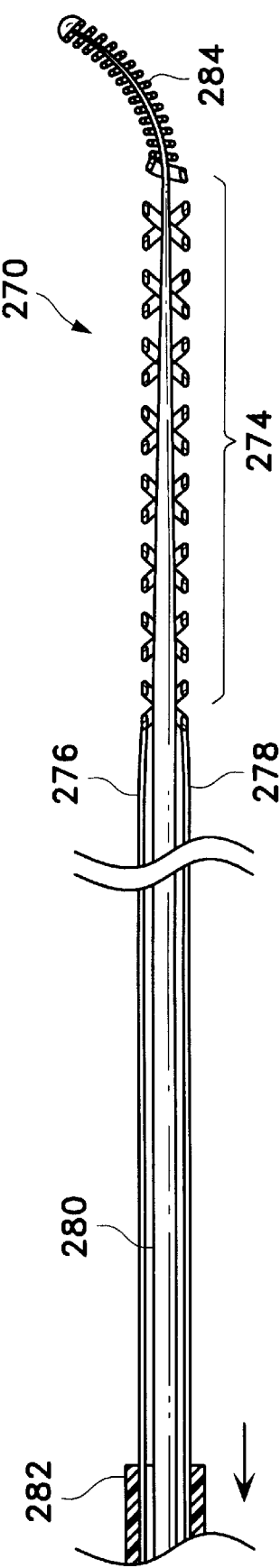
Fig. 4A
Fig. 4B

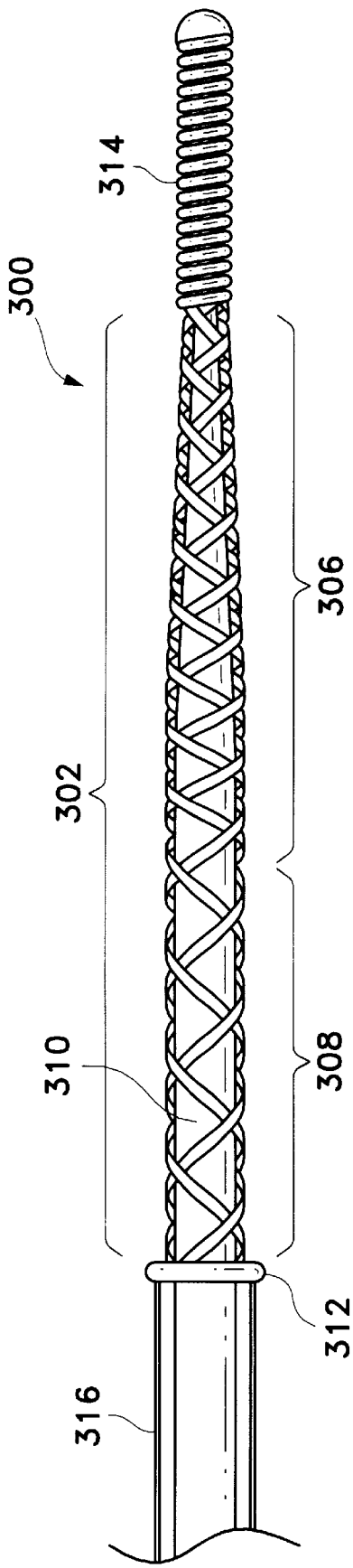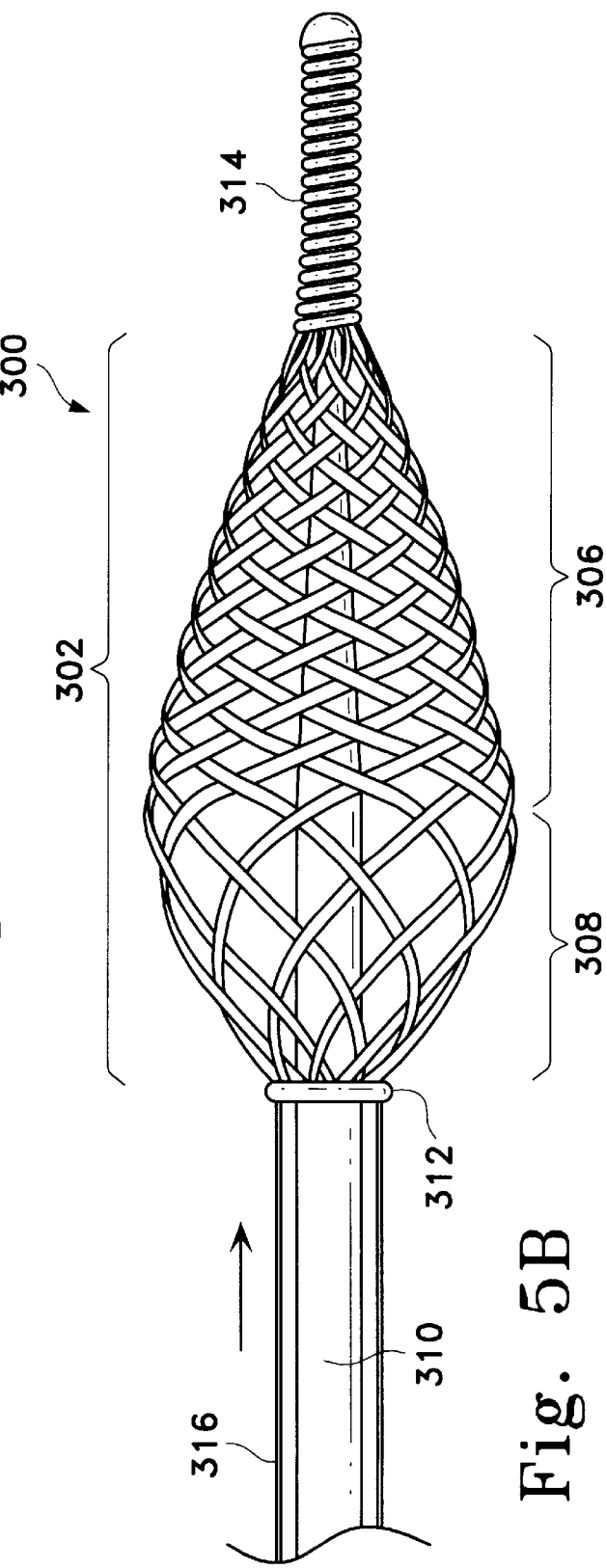

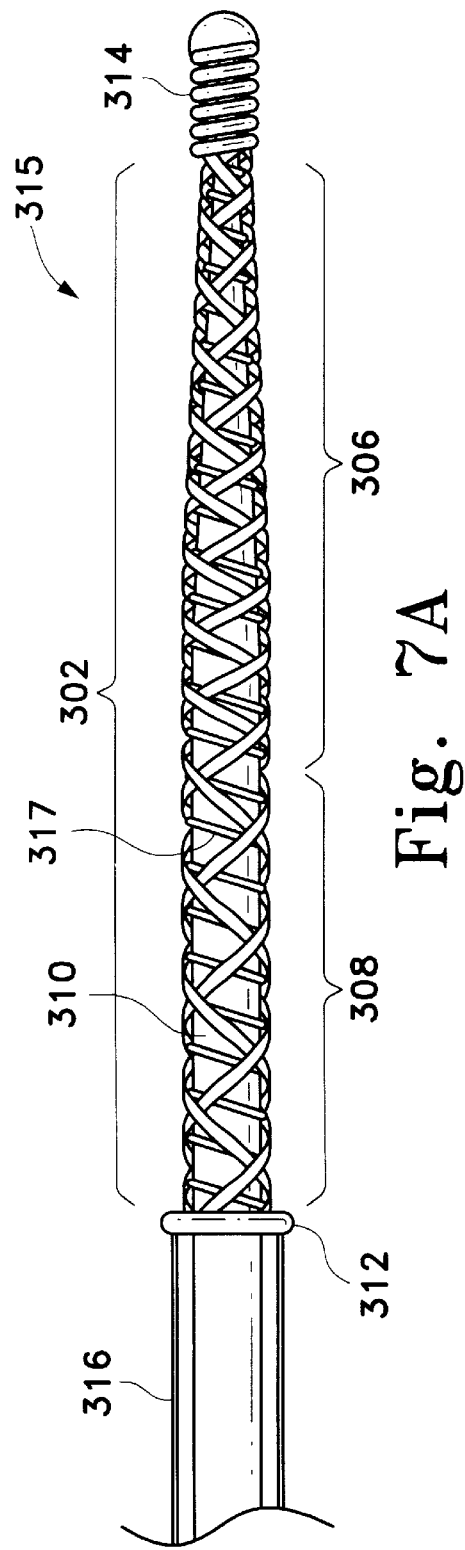
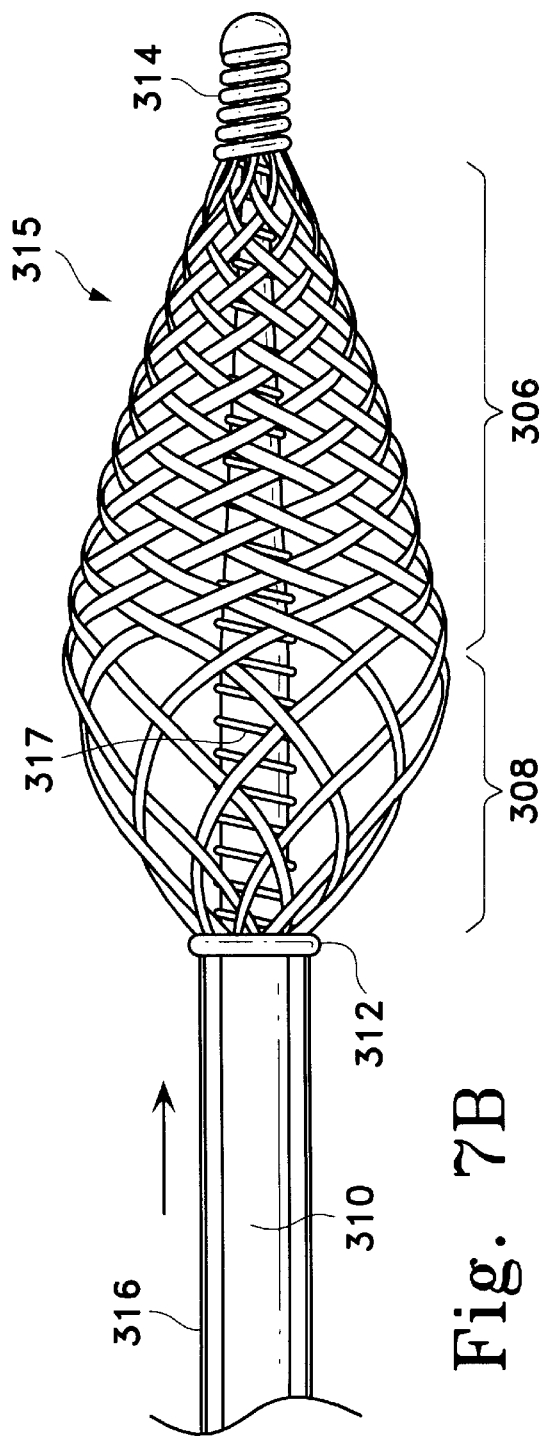
Fig. 7A
Fig. 7B

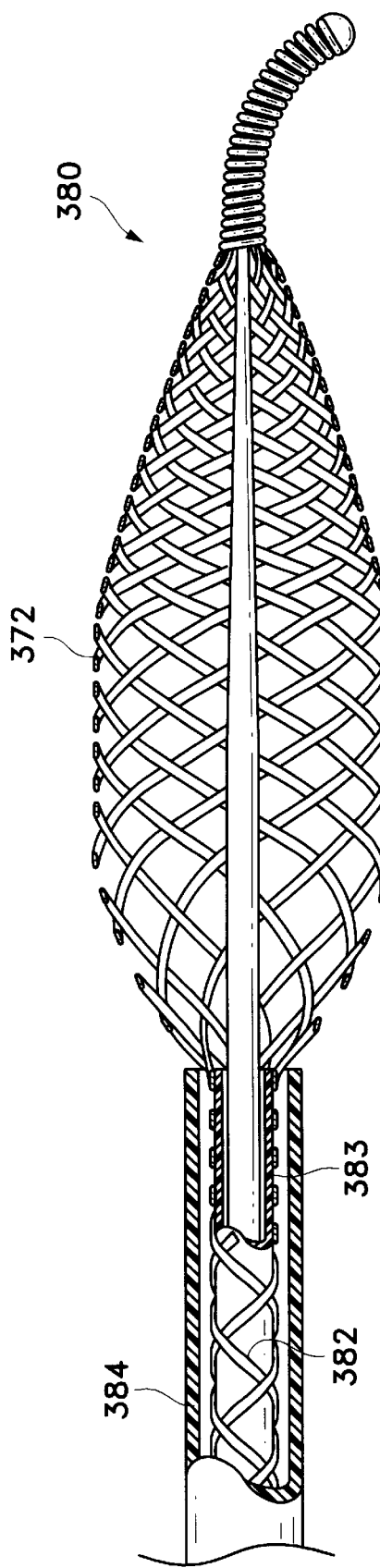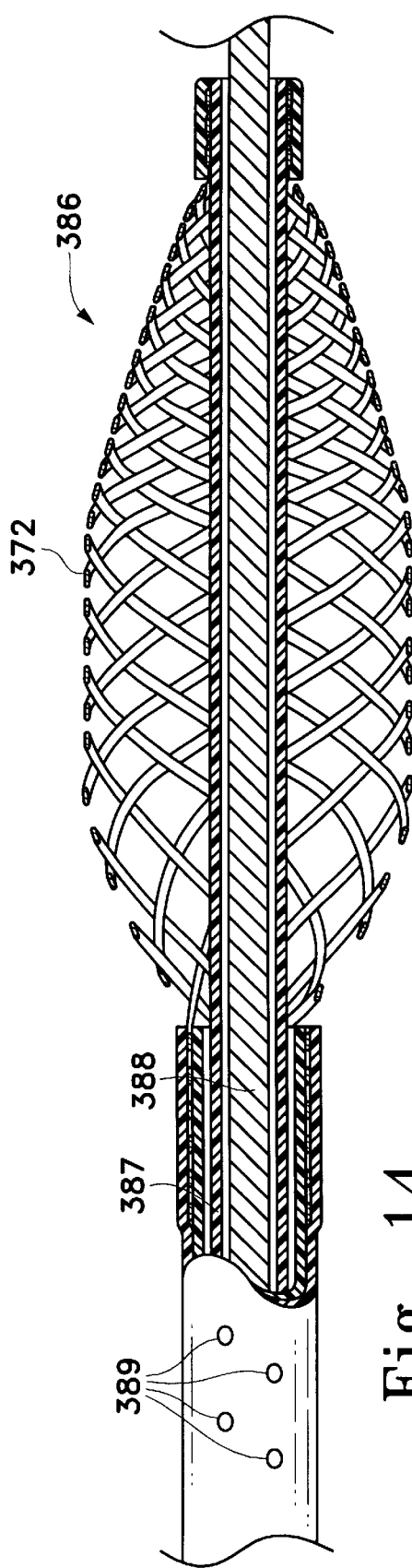
Fig. 13
Fig. 14

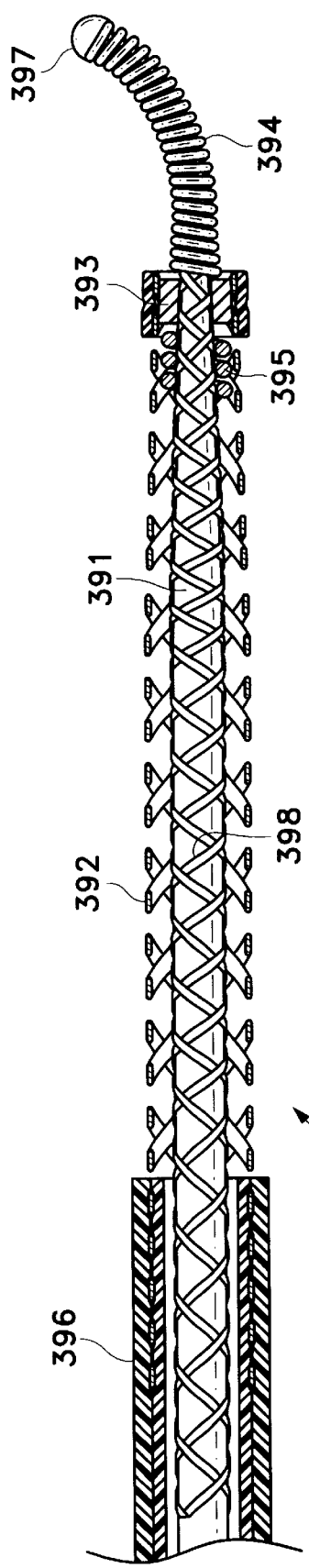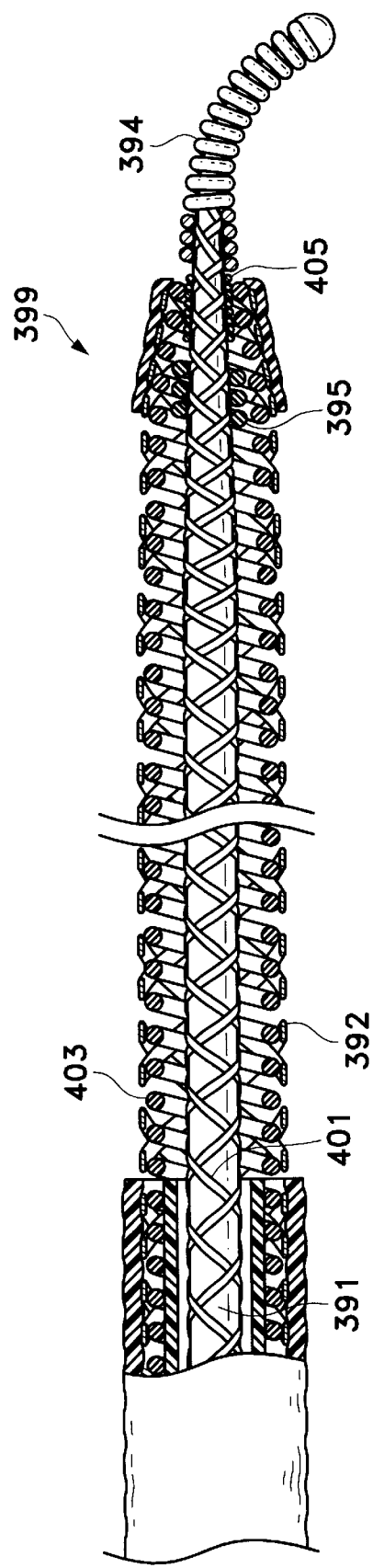
Fig. 15A
Fig. 15B

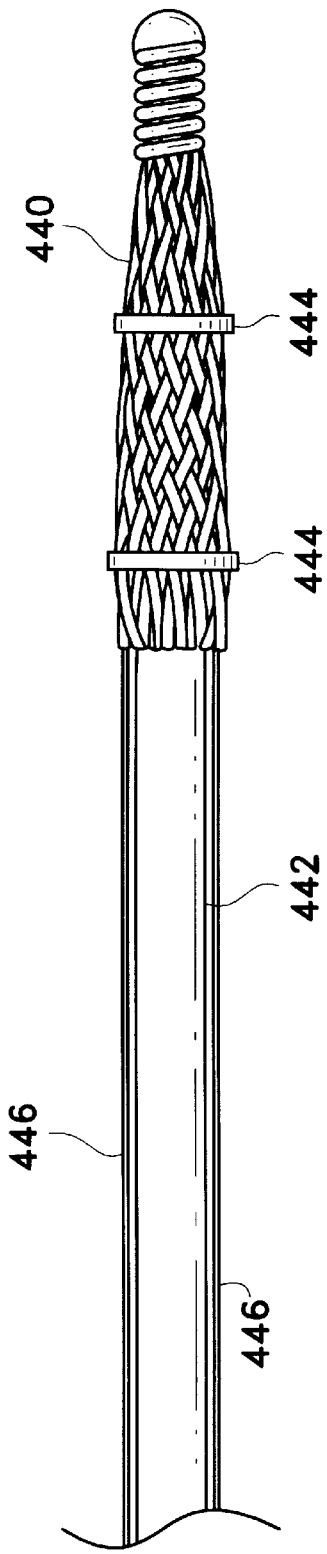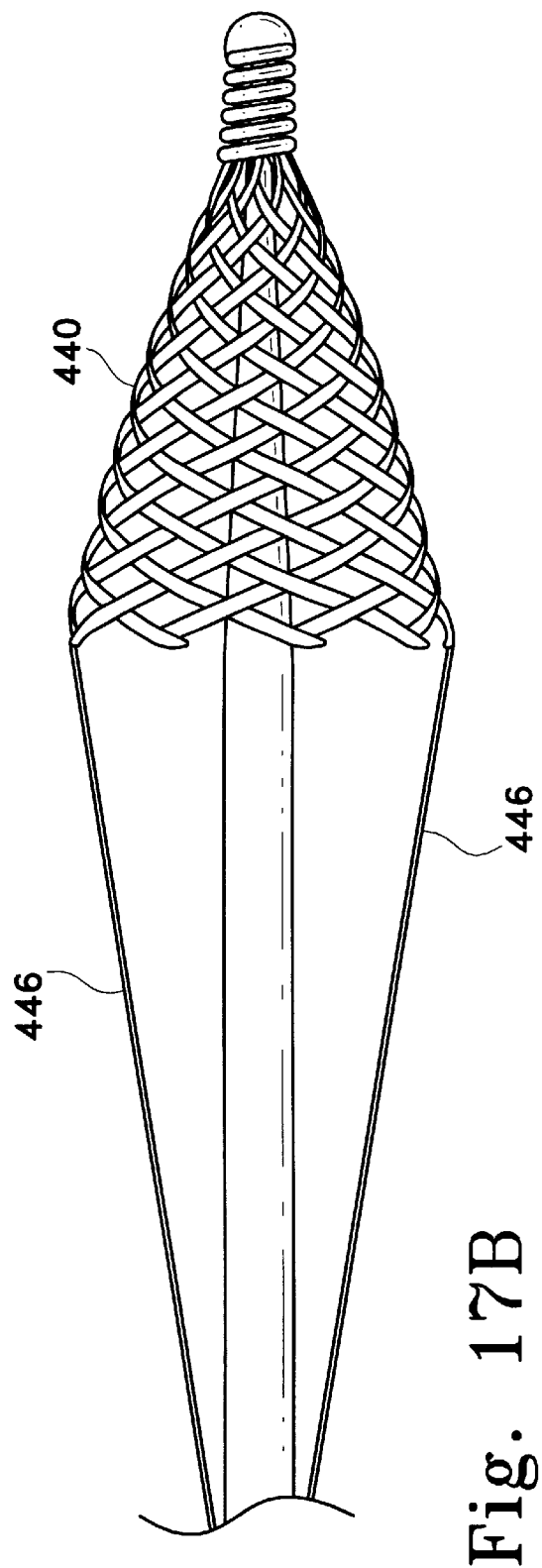

MECHANICAL CLOT TREATMENT DEVICE

RELATED APPLICATIONS

This is a continuation-in-part of U.S. Ser. No. 08/686,304, filed Jul. 25, 1996 entitled "MECHANICAL CLOT ENCASING AND REMOVAL WIRE" and of U.S. Ser. No. 08/701,155, filed Aug. 21, 1996, and abandoned on Jan. 29, 1998 entitled "MECHANICAL CLOT ENCASING AND REMOVAL DEVICE WITH OPTIONAL ROTATABLE GUIDEWIRE" the entirety of which are incorporated by reference.

FIELD OF THE INVENTION

This is a medical device. In particular, it is a surgical device usually delivered thtrough an intravascular catheter. It may be used in several ways. It may, for instance, be used to open a clear passageway adjacent thrombus to allow both blood and medication to bypass the clot. It may be used to pierce and to remove thrombus. These thrombus are often found in tortuous vasculature. The device includes several sections. The device has a core element, typically a core wire. Placed around the distal end of the core element is a collapsible but preferably self expanding cage assembly. The cage assembly is preferably radio-opaque. The proximal end of the cage is typically is affixed to an actuator in such a way as to allow expansion of the cage after deployment. The cage assembly may have a generally conical distal or "trailing" portion when expanded and also a proximal section. The cage assembly may be used for collecting emboli or for displacing them to allow blood flow to resume, either with or without concurrent clot-dissolving drug treatment. The proximal section may have various uses, e.g., for centering the collector assembly in the vascular lumen or for gathering larger amounts of the targeted clot or to act as a passageway for fluid flow. The assembly further may have an actuator which permits or causes the collector assembly to expand after deployment.

BACKGROUND OF THE INVENTION

This surgical device is designed to displace or to penetrate emboli found in the human vasculature. Depending upon the chosen procedure, it is inserted into the region either towards the venous side of the clot or adjacent the clot. The cage is expanded either to displace the clot from the arterial wall and allow flow of fluid (i.e., blood and medications such as anti-thrombolytics or other lysing agents) past (or to) the formerly occluded site or to engage the clot for removal using the cage as a collector assembly, expand once past the target emboli, and catch or net the embolism (or a portion of the embolism) for removal from patient's blood vessels. In some situations, the device may be used to move the clot to another position in the vasculature; perhaps for recovery using another device or to canalize the clot for improved blood flow.

The use of inflatable balloons to remove emboli has been practiced for many years. The "Fogarty catheter" has been used, typically in the periphery, to remove clots from arteries found in legs and in arms. These well known devices have been described in some detail in U.S. Pat. No. 3,435,826, to Fogarty and in U.S. Pat. Nos. 4,403,612 and 3,367,101. These patents describe a balloon catheter in which a balloon material is longitudinally stretched when deflated.

Emboli occasionally form around the valves of the heart and then are dislodged and follow the blood flow into the distal regions of the body. They are particularly dangerous if the emboli passes to the brain and causes an embolic stroke. As will be discussed below, many such occlusions occur in the middle cerebral artery (MCA), although such is not the only site where emboli come to rest. Obviously, when blood flow is inhibited or cut off completely from a portion of the brain, the brain's oxygen supply is limited causing severe problems.

In procedures for removing emboli using the Fogarty catheter or other similar catheters, it is typical, first, to locate the clot using fluoroscopy. The embolectomy catheter is then inserted and directed to the clot. The distal tip of the balloon catheter is then carefully moved through the center of the clot. Once the balloon has passed through the distal side of the clot, the balloon is inflated. The balloon catheter is then gradually and gently withdrawn. The balloon, in this way, acts to pull the clot ahead of the balloon. The majority of procedures using a Fogarty catheter repeat these steps until the pertinent vessel is cleared of clot material.

Such vaso-occlusions occur in a wide variety of sites within the body. The lodging of thrombus in various sites is complicated by the presence of atherosclerosis. This disease causes the vessels to become tortuous and narrowed. These anomalies are often considered to be the result of the growth of atherosclerotic plaque. Clots occurring in these diseased vessels are difficult to remove using balloon or Fogarty catheters.

Removal of emboli using balloon catheters is rife with potential problems. One such problem occurs during removal of a clot. The resistance to such removal often causes the balloon portion of the catheter to evert over the tip of the catheter. Should the user need to partially deflate the balloon during such a deflation, the distal tip of the balloon may become distended and angulate. Another difficulty with balloon catheters is the possibility of damage to the intima of arteries. Inflation pressures can create forces significant enough to shaer such a vessel lining or dislodge plaque lodged on such a wall. In the worst case, the balloon may rupture leaving balloon portions in the bloodstream.

Movement of a balloon in the MCA using only a balloon can displace the clot through more proximal branches into other large vessels such as the internal carotid artery (ICA) and then into other vessels.

There are a variety of different devices intended for use in replacing balloon catheters and in using a device other than a balloon catheter in so removing the emboli.

One such device is shown in U.S. Pat. No. 4,030,503 to Clark III. This patent describes a spiral helix affixed to the distal end of a catheter. In particular, the spiral helix is designed to be rotated and pushed forward through the clot. It is said that the helix screws into the clot, and when it is firmly embedded or is past the clot, the catheter is pulled out of the vessel without rotation. The catheter is said to operate like a corkscrew.

A similar catheter is described in U.S. Pat. No. 4,706,671 to Weinrib. This catheter also has a coil section at its distal end. The coil section is said to be stretched initially into a generally linear insertion position for removing inwardly in a vessel. The coil member is then expanded into the form of a hollow conical scoop to then scoop clot material from the blood vessel. The coil member is stiffened by an internal wire which is then removed. The hollow passageway is then filled with a liquid to stiffen the coils. The coils are said to be of an elastomeric material.

U.S. Pat. No. 4,762,130 to Fogarty et al., describes a helical balloon attached to the distal end of a catheter. The helical or bellowed balloon is maintained in a generally linear condition and passed into a clot. Once the catheter balloon within the clot is inflated, the balloon and adjoining clot are removed together.

Another similar device used more to grip and shear atherosclerotic deposits rather than to remove thrombi is described in U.S. Pat. No. 4,890,611 to Monfort et al. This device incorporates a pair of helical wires placed on the distal end of a wire. The flexible wire is pulled against a flexible catheter and the two helically configured loops expand to form a shearing apparatus. The totality of the apparatus is then twisted by means of a handle so that the pair of helically wound loops cuts through and is said to retain sections of plaque for removal from the vessel under treatment.

Another thrombus extraction system is shown in U.S. Pat. No. 5,011,488, to Ginsberg. In this device, an inflatable balloon having a proximal conic shape is deflated and passed through a thrombus. It is then expanded and retracted so that the proximal passage pulls the thrombus into contact with an aspirator. The aspirator then removes the clot or thrombotic material from the vessel.

An alternative configuration of the expandable member is also described in the Ginsberg patent. In this variation, a wire coil is attached to an extension wire which may be moved between an extended position and a retracted position. The retracted or expanded configuration is illustrated to have a conical shape. The cone is shown to be one which has a smaller end proximally.

U.S. Pat. No. 5,112,347, to Taheri, shows an inflatable balloon type embolectomy catheter. The balloon has a number of fingers arranged in a leaf spring arrangement inside the balloon. The balloon is hydraulically inflated and forms a cone after inflation. The deflated device is shown in FIGS. 11 through 14 to be passed distally past an embolism before inflation. After inflation, the large end of the balloon collects the embolism as it is pulled past the appropriate site in the vessel.

U.S. Pat. No. 5,192,286, to Phan et al., shows a retrieval catheter for removing materials from various body lumens. The retrieval catheter is shown to have a slack net which may be collapsed for passage into lumen past the material to be collected. The net is unfolded after such passage and materials such as uretral stones are removed.

U.S. Pat. No. 5,411,509 to Hilal, shows an embolectomy catheter having an elastomeric foam tip attached distally. The foam tip has an actuator means suitable for forming the foam section both longitudinally and radially in response to activation of the actuation. In practice, the catheter tip is pressed past an embolism, inflated, and retracted with the clot being pushed proximally as retraction occurs.

U.S. Pat. No. 5,490,859, to Mische et al., shows an intravascular occlusion material removal device having an expandable material removal element made up of a number of wires passing between the two ends of such element, a catheter shaft, a drive shaft for spinning the material movement element within the blood vessel, and a collection portion placed on the material removal element for collecting any occlusion material removed by the expandable material removal element. The drive shaft may be operated by a motor connected to the drive shaft proximate to the proximal end of the drive shaft.

None of these devices approximates the design of the device described below.

SUMMARY OF THE INVENTION

This is a surgical device usually delivered through an intravascular catheter. It is designed variously to displace or to pierce and remove emboli particularly when found in tortuous vasculature.

This embolectomy device includes several sections. First, the device has a core element. The core element preferably has at least several major functions: first, the distal portion acts as a guidewire for vessel navigation to the treatment site; second, the distal portion assists in puncturing of the clot; and third, it cooperates with the collection assembly during the deployment of that assembly. The core element may be a simple core wire (perhaps enhanced with an adherent braid) fixedly attached to the distal end of the cage assembly or a tubular member attached to the collection assembly having a removable core or guidewire in its interim. Preferably, the core element is able to rotate freely with respect to collection assembly to preserve its abilities as a guidewire while preserving the cage assembly shape and integrity. Placed distally on the core element is a collapsible (but desirably) self expanding cage assembly. That cage may be fixedly or rotatably joined to the core wire at the embolism collection assembly's distal end. The cage may have a generally conical distal portion when expanded and a proximal section having varied purposes, e.g., for centering the cage assembly in the vascular lumen and providing a receptacle for entrapment of the clot. Most preferred of the designs for the cage assembly involves a super-elastic alloy ribbon or wire braid.

The assembly further may have an actuator which permits or causes the collector assembly to expand after deployment. The actuator may be mechanical in nature or electrolytic, or may include a balloon. When the actuator is mechanical, it is typically attached to the proximal end of the cage assembly to allow or cause controllable expansion of the cage assembly.

BRIEF DESCRIPTION OF THE DRAWINGS

FIGS. 3A and 3B show, respectively, a side, cut away view of a spiral version of the device as expanded and as unexpanded.

FIGS. 4A and 4B show, respectively, a side, cut away view of a double spiral version of the device as expanded and as unexpanded.

FIGS. 5A and 5B show, respectively, side views of a braided version of the device as expanded and as unexpanded.

FIGS. 7A and 7B show, respectively, side views of a braided version of the device as expanded and as unexpanded having spring-assisted deployment.

FIG. 13 shows a further variation and partial cross section having a braid supported tubular actuator.

FIG. 14 shows in cross section a variation of the inventive device in which the core assembly comprises a tubular member attached to the distal portion of the cage element and having a freely moving core wire passing therethrough.

FIGS. 15A and 15B are close up partial cut away side views of distal tips of the inventive device showing rotatable core assemblies.

FIGS. 17A and 17B show a variation of the inventive device using an electrolytically erodable link as a means for allowing expansion of the included cage element.

DESCRIPTION OF THE INVENTION

This device is a surgical implement. It is designed variously to move a thrombus aside and provide a fluid passageway along that thrombus or to penetrate and at least partially to retrieve emboli situated in human vasculature. It is intended to be used rapidly as a flow restoration device. Even in those instances where the embolism is not or cannot be completely removed, this inventive device is believed to be useful in displacing, extracting, or removing a portion of the clot and thereby permitting restoration of partial blood flow. It can be used to move the clot to a more advantageous site in the body. It is suitably flexible to be placed in the distal tortuous vasculature of the brain and hence is useful in treating blocking emboli found there. This device can be thought of as a partial treatment for embolic stroke.

Figure 1:
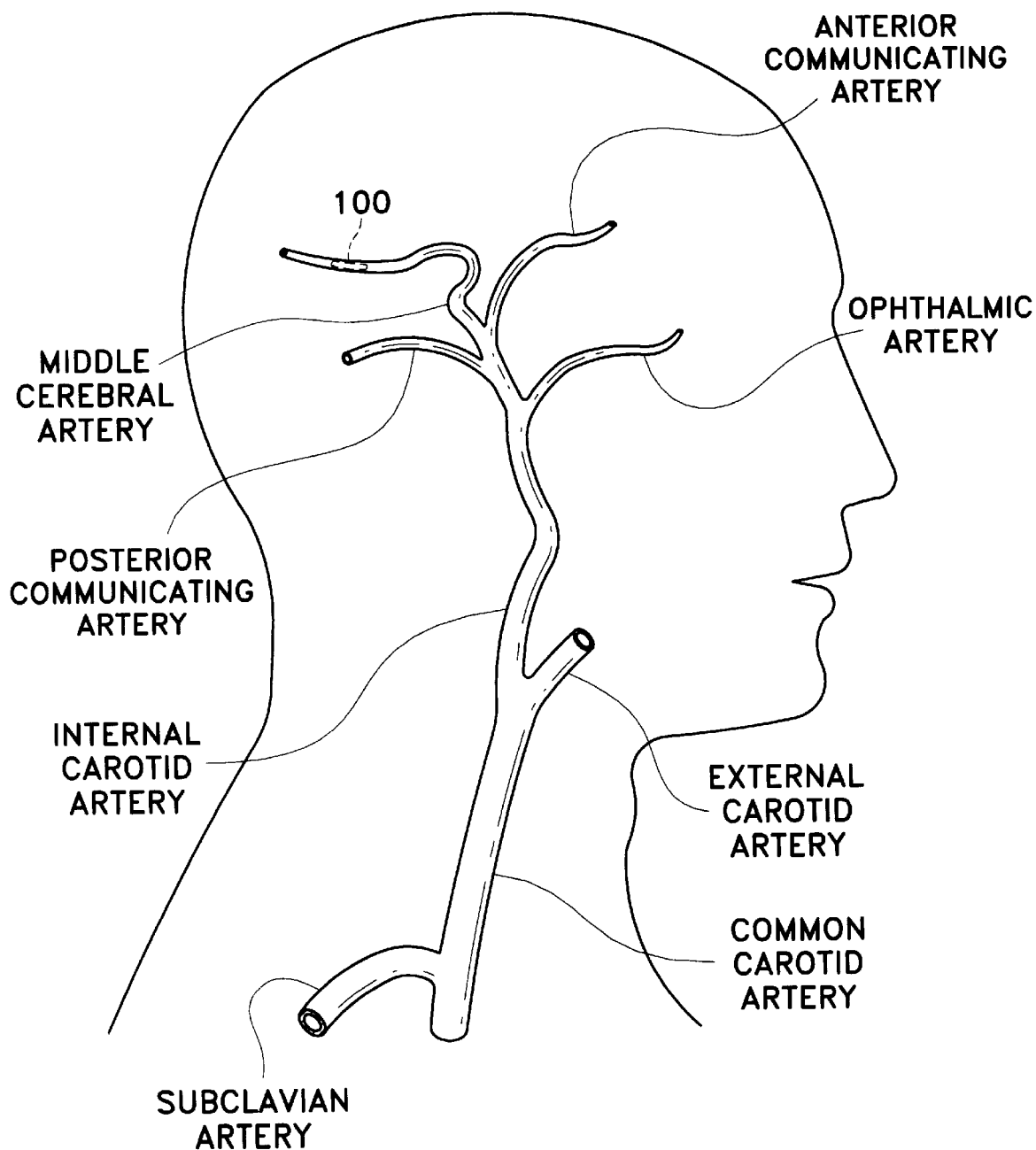
FIG. 1 shows a generalized schematic of a portion of the arterial system of the head specifying in particular the position of an embolism in the middle cerebral artery.

As a matter of practical experience, a large proportion of emboli sloughed into the brain are seldom longer than about 1 to 2 centimeters and, for a variety of reasons both physiological and hemodynamic, settle in the middle cerebral artery (MCA). As is shown in FIG. 1, the path from the site of origin of a traveling embolus—often the heart—to the MCA is via the common carotid artery past the branch point forming the external and internal carotid arteries into the internal carotid artery (ICA). The MCA is generally considered to be the continuation and termination of the ICA after the siphon and after the branching sites of a variety of other arteries, e.g., the ophthalmic artery, the anterior communicating artery, the posterior communicating artery, and others. The etiology of such an occlusion is varied, varying, and complicated. The occlusion (100) is shown in the MCA in FIG. 1 at the noted site.

Treatments for such embolic occlusions include catheterization of the patient and introduction of tissue plasminogen activator (TPA) or urokinase to the site of the occlusion. Additionally the embolic occlusion may be penetrated—often with a microcatheter—and the TPA or urokinase introduced distally of the occlusion. Removal of the catheter provides a modest passageway for resumed or increased blood flow past the then-partial occlusion.

This inventive device is for the rapid restoration of fluid or blood flow past the occlusion. We have found that it can be used in a variety of ways. For instance, when approaching the clot from the arterial end, the device can be used either to bypass the clot along the vessel wall and, upon expansion of the cage assembly, to allow flow of blood across the occlusion using the cage assembly as a fluid passageway.

Alternatively, inventive device may be used to canalize or remove an occlusion, via the steps of penetrating the occlusion, expanding a cage assembly distally of the embolism, and preferably removing at least a part of the embolism along with the cage and its attendant catheter.

Figure 2:
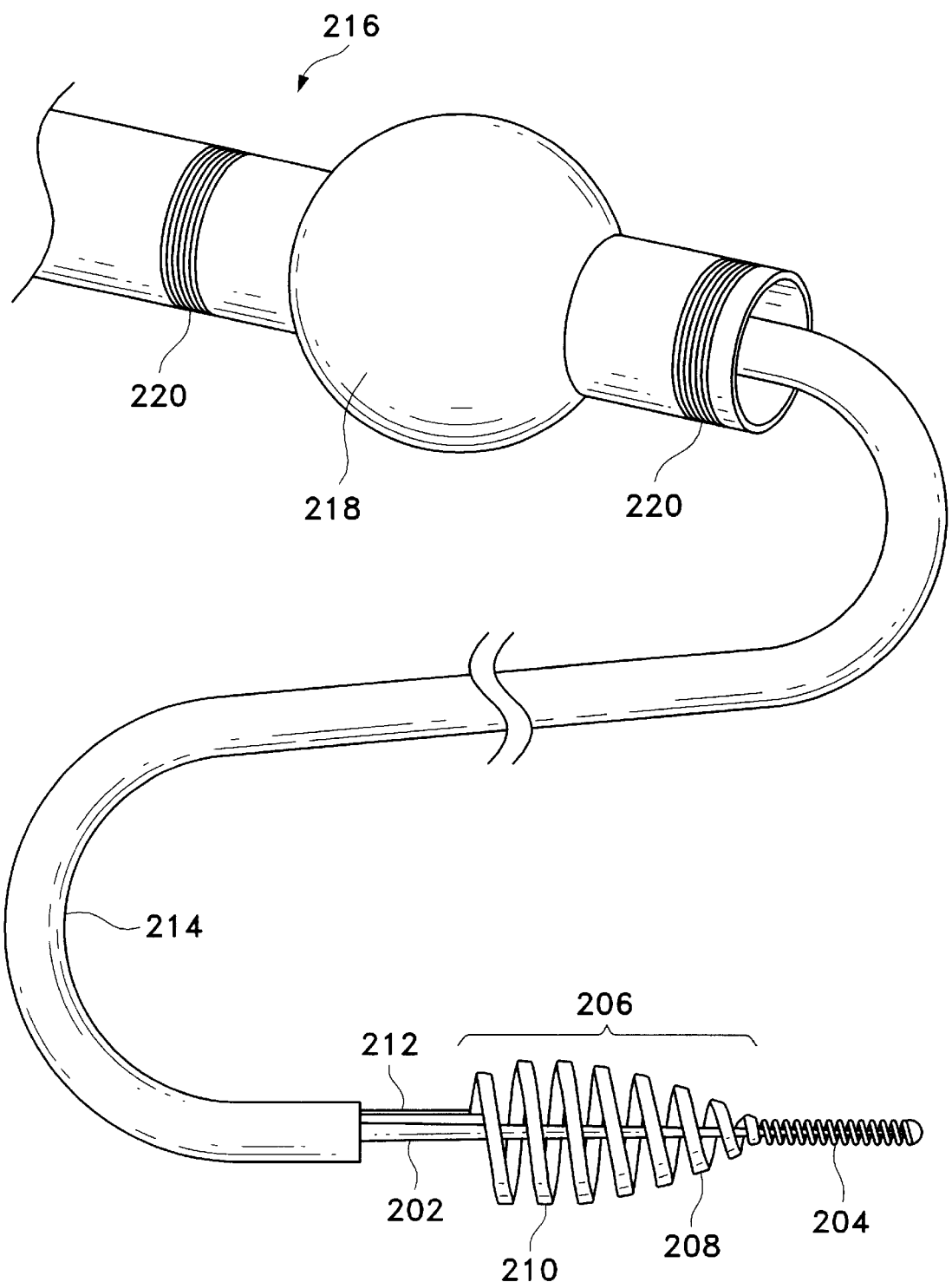
FIG. 2 is a partial view of a catheter and a generalized rendering of the inventive device.

FIG. 2 is a diagrammatic portrayal of the major portions of a desired variation of the device and provides a general convention for several of the terms used herein.

The assembly typically includes a core element, often a core wire (202), and optional coil tip (204) to provide a measure of radio-opacity to the distal tip and protect against damage to the intima, and a cage assembly or element (206) which may be used as an embolism collector made up of a generally conical portion (208) having a decreasing radius and an optional cylindrical portion (210). Because of the "fineness" of the device, the coil tip (204) may also serve the same function as a guidewire tip. The length of the coil tip (204) may be up to 4 or 5 centimeters in such cases. Further, and as is discussed below, the core element may be an assembly comprising a tubular member further containing a removable core or guidewire. The cage assembly (206) is collapsible for passage along-side of or for penetration and passage through the embolism and is generally self expandable once it passes the embolism. Other procedures and devices may, obviously, be used to expand the cage assembly (206) and are discussed at some length below. The cage assembly (206) generally self-expands when the actuator element (212) is permitted to move from its introduction position to its deployment position. Attached proximally to the actuator element (212) is a sheath (214) extending back to the catheter assembly (216) to the person performing the procedure. The catheter assembly (216) is shown with an optional micro-balloon (218) which may be useful in some embolectomy procedures, and two radio-opaque bands for the purpose of allowing the user to visualize the tip of the catheter (216) in relation to the tip coil (204) in the embolism to be removed.

FIGS. 3A and 3B show cross-sectional side views of a variation of the inventive device (250). This variation of the inventive device (250) includes a cage assembly (252) having a distal conical portion (254) and a cylindrical portion (256). The distal end of the distal conical portion (254) is fixedly attached to the core wire (258). Attachment may be by any convenient procedure, e.g., soldering, welding, gluing, etc. A preferred structure for such tip coil (258) is discussed below.

The cage assembly (252) is preferably made of a superelastic alloy wire or ribbon. Some stainless steels are suitable but the ready availability of nickel-titanium alloys in a wide variety of shapes and sizes makes this choice an easy one. In particular, we have found that ribbons as thin as 0.75 mils in thickness and as narrow as 2 mils in width are suitable for this device. Thicker and wider ribbons are also suitable in some instances as the situation requires. Preferred ribbons for the cage assembly (252) are between 0.75 and 1.5 mils in thickness and 3 and 7 mils in width. Most preferred are 0.8 mils and 4 mils respectively.

A technical basis for the term "super-elastic" is found in the class of nickel-titanium alloys known as "nitinol"— alloys discovered by the United States Navy Ordnance Laboratory. These materials are discussed at length in U.S. Pat. Nos. 3,174,851 to Buehler et al; 3,351,463 to Rozner et al; and 3,753,700 to Harrison et al. Alloys especially suitable for this invention are those containing at least 1.5% (wt) and up to about 8% (wt) or more, of one or more alloying members selected from the group consisting of vanadium, chromium, manganese, iron, and cobalt. By the term "ribbon", we intend to include elongated shapes, the cross section of which are not square or round and may typically be rectangular, oval, or semi-oval. They should have an aspect ratio of 0.5 (thickness/width) or less.

The cage assembly (252) may be made by winding a ribbon onto a mandrel having exterior form to produce the relaxed shape found in FIG. 3A. The mandrel and wound ribbon are preferably heated for a suitable period of time (e.g., 750° to 1200° F. for one-half to two hours) to produce an embolism cage assembly (252) which has the portrayed shape. For use in the MCA, the outer diameter of the device after deployment need not be any larger than about 3 mm. It is desirable that the collapsed or non-deployed device have a diameter no larger than about 1 mm. The expansion ratio between any of the deployed and deployable devices discussed herein typically need not be any more than about 3:1 to be effective in the MCA. Expansion ratios between 2:1 and 10:1 are appropriate in this invention. These ratios are suitable for each variation of the invention. The invention is not so limited, however.

The actuator (260) may be independently produced from the cage assembly (252) or may be produced integrally with it. The sleeve (262) is attached, as appropriate, to the actuator (260). Each of the cage assemblies shown herein may also be made using wires rather than ribbons. By "wires" we mean to include filamentary shapes having cross-sections where the thickness/width ratio is greater than 0.5 to and including 1.0. The cross-sectional form may be circular, square, oval, etc.

The cage assembly (252) is displayed in a relaxed or deployed condition in FIG. 3A. Because the cage assembly (252) desirably is springy and self-expanding, it is allowed to expand solely due to the position of the actuator (260). In the actuator (260) position shown in FIG. 3A, the cage (252) assumes the "relaxed" position. When the actuator (260) position is as shown in FIG. 3B, the cage assembly (252) is pulled within close proximity of the core wire (258). The distal coil (204) is also shown in FIGS. 3A and 3B. FIG. 3A shows the form of the device as it passes through the delivery catheter and is pressed through the embolism. The low profile or small cross-sectional area of the device (250) is apparent.

In some designs of the device, it is permissible to use the actuator as an active deployment element rather than as a mere restraint on the premature expansion of the cage assembly.

FIGS. 4A and 4B show a cross section of another variation of the inventive device related to that variation found in FIGS. 3A and 3B but employing a slightly more complicated cage assembly.

In particular, FIG. 4A shows an inventive device (270) having a pair (272, 274) of counter-wound ribbons serving as the cage assembly (276), each of which counter-wound ribbon (272, 274) is similar in construction and in materials of construction to cage assembly (252) in FIGS. 3A and 3B. Clearly the associated elements such as actuator (276, 278), core wire (280), actuator sheath (282), distal coil tip (284) are all similar in construction and use to the analogous parts found in FIGS. 3A and 3B. The variation shown in FIGS. 4A and 4B generally have the detriment of being somewhat thicker (or of a larger diameter) than the variations shown in FIGS. 3A and 3B. On the other hand, it may be expected to have a marginally higher spring rate and therefore self-expand more readily. The probability that the deployed device is centered in the chosen lumen is higher in the FIG. 4A and 4B version as is the probability that it will collect a higher percentage of the errant embolism.

As a matter of practicality, however, the usual path to a position venous of the embolism will be along the wall of the artery. Consequently, an ability to center in the vessel lumen is useful when the device is used primarily for removal of the clot rather than for merely its displacement.

FIGS. 5A and 5B show a further version of the inventive device (300) in which the simple cage assembly comprises instead a braid. These depictions are in side view.

As may be seen in FIG. 5A, when the braided cage assembly (302) fits tightly around the core wire (310) two regions (306, 308) are of differing ribbon spacing. The more distal conical section (306) is woven into a comparatively tighter weave than is the more proximal section (308). There are reasons for this difference. As may be seen in FIG. 5B, the tighter weaving in the distal section (306) is for the purpose of catching emboli particles which have passed through the larger windows of the proximal ends (308) of the cage assembly (302).

The ribbons making up the braided embolism cage assembly are preferably of the super-elastic alloys discussed above. A minority of the ribbons may be a suitable stainless steel (e.g., 304SS, 306SS, etc.) or other such alloy. A desirable variant is the substitution of one or more ribbons of the braid (or the addition of one or more ribbons) with a radio-opaque material such as platinum. This obviously permits the user to visualize the position of the embolism cage assembly (252) during the clot removal procedure.

FIG. 5B shows another overall exterior profile of the cage assembly (302). The distal section (306) is not shaped in the same linear cone aspect depicted in the earlier Figures. It should be noted that those earlier variations need not be linear as is shown there but may be curved in many different shapes. By "conical" or "cone" we mean simply that the tubular member forming the various embolism cage assemblys has a diameter which is larger at some position along the axis of that embolism cage assembly than at the site where it joins the core element but without regard to the outer profile of the element. That is to say that the profile of the embolism collector assembly element is not otherwise limited. The profile may be linear, curved, stepped, etc.

Returning to the Figures, FIG. 5B depicts the cage assembly (302) after deployment. A desirable, but not a necessary, component of the assembly is the proximal ring (312). Proximal ring (312) slides axially on core wire (310) and may be fixed or attached to the ribbons of the braided cage assembly (302). Such fixed attachment enhances the tendency of the cage assembly (302) to regain its relaxed shape, it also helps maintain the deployed device in the center of the vessel lumen. Alternative structures for the actuator assembly are discussed elsewhere.

The remainder of the components shown in FIGS. 5A and 5B, e.g., distal coil (314), actuators (316), etc., operate in the same way as the analogous components in the versions discussed above.

Figure 6A:
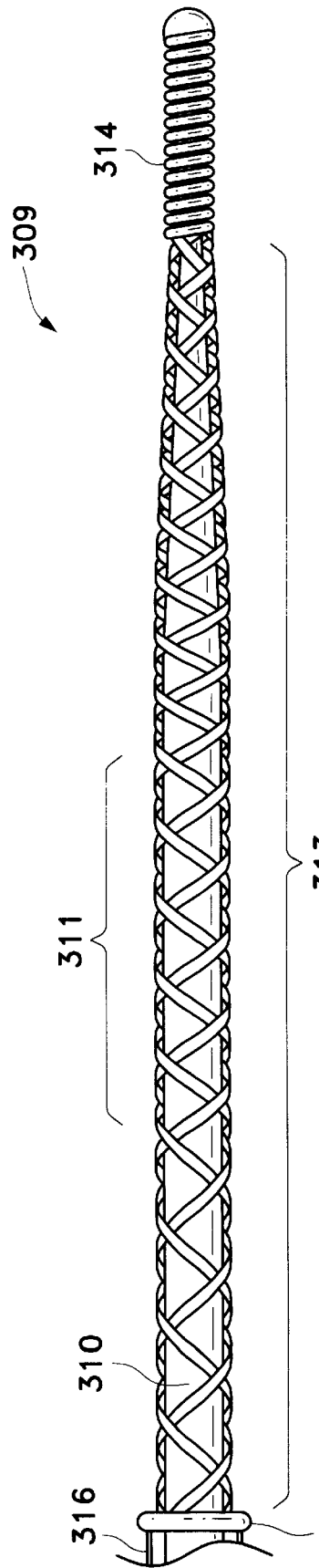
FIGS. 6A and 6B show, respectively, side views of a braided version of the device having a cylindrical mid-section as expanded and as unexpanded.
Figure 6B:
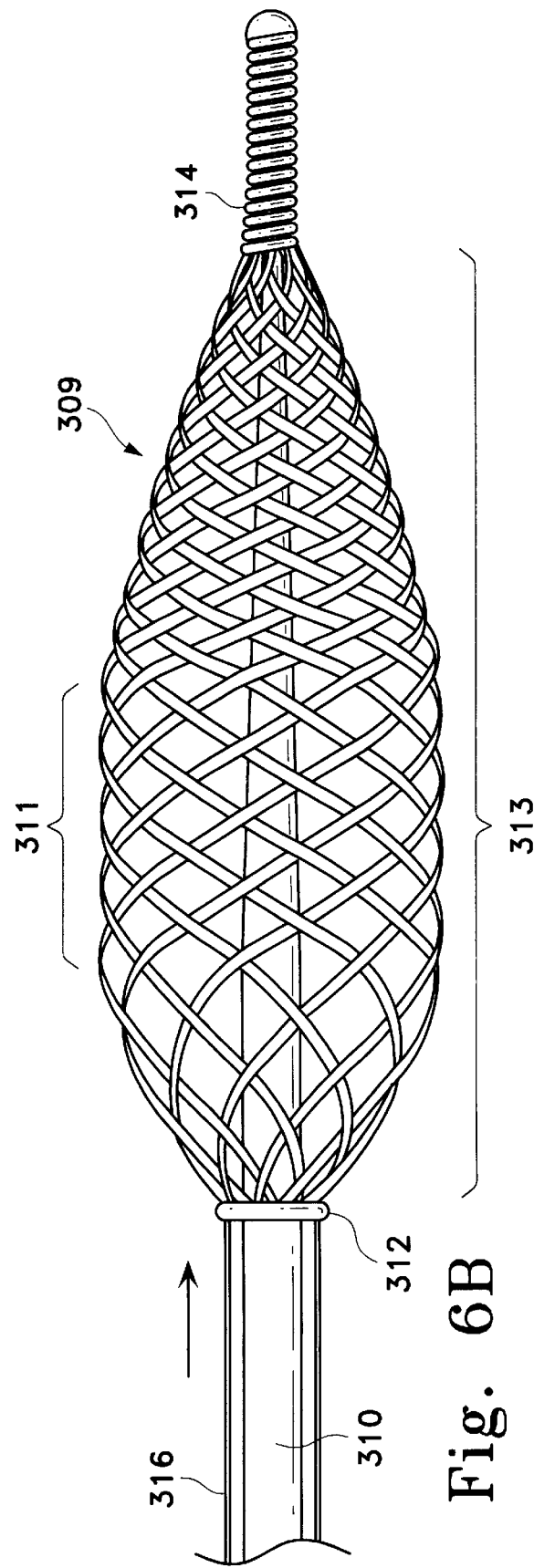

FIGS. 6A and 6B show a variation (309) of the invention shown in FIGS. 5A and 5B having a mid section (311) in the braided cage assembly (313). FIG. 6B shows the profile of the braided embolism collector assembly (313) after deployment of the device. This profile allows more predictable centering of the assembly in the vascular lumen after the noted deployment. As is the case with the other designs, this variation may be used in a smaller size to "core" an embolism rather than to remove the whole occlusion.

This shape of braided cage assembly (313) is preferred for small vessel embolectomies. We have found that when using this device in a self-deploying variation, having a mid section (311) causes the embolism collector assembly (313) to self-deploy with greater ease than with many of the other variations described here.

FIGS. 7A and 7B show still another variation (315) of the inventive device. This version is of the same general configuration as is found in FIGS. 5A, 5B, 6A, and 6B in that it relies upon a multi-spacing braid as the cage assembly (302). The aspect of the invention to be shown in this variation is the presence of coil (317) generally along the exterior surface of the core element (310). This spring coil (317) in this figure is selected to be relaxed in the profile shown in FIG. 7B and, conversely, is in a stretched, tension condition n FIG. 7A. The spring coil (317) is attached to the cage assembly (302) at both its distal and proximal ends so that when the coil (317) is released, it aids the self-expanding cage assembly (320) to expand to the deployed condition shown in FIG. 7B even if the device is within the embolus. Actuator lines (316) also may be used as safety means to collapse the collector assembly (302) should the deployment be non-advantageous. Actuator lines (316) also may be used to control the rate of spring-aided deployment expansion if such control is desired.

We further contemplate the use of a spring which is relaxed (or under slight tension) prior to deployment and under compression after deployment. The actuator assembly is then used to press open and deploy the collector assembly.

Figure 7C:
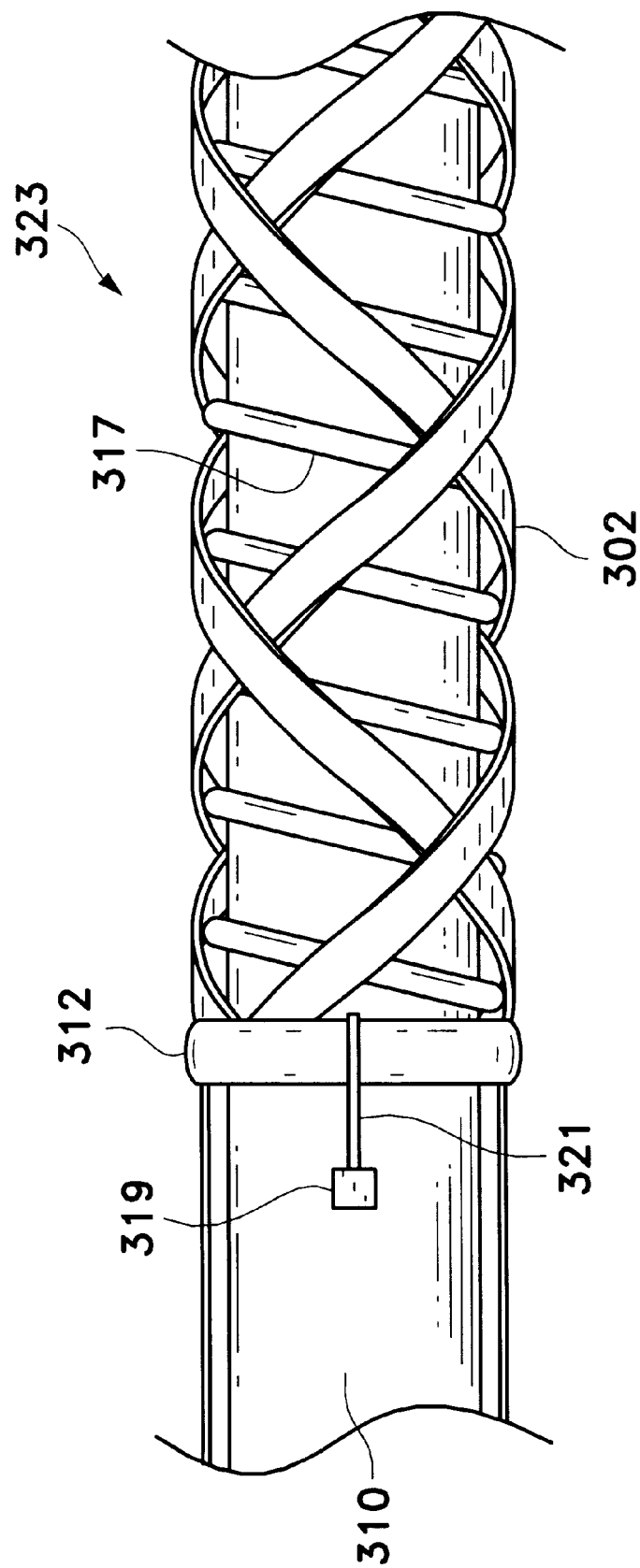
FIG. 7C shows an electrolytically severable joint for the deployment of the device shown in FIGS. 8A and 8B.

FIG. 7C shows a close-up of a portion of one of the braid versions discussed above. Although the spring (317) of FIGS. 7A and 7B is shown, it is only optional in the discussion of the release feature shown here. This Figure details an exempletive electrolytically deployable version of this invention. Specifically, the embolism collector assembly (302) is under contained tension as shown in FIG. 7C. Either or both of the cage assembly (302) and spring (317) are in a position to expand the cage assembly (302) were it not for the presence of the link (321). In this version, the link (321) is electrically attached to the core wire (310) through connecting site (319). It should be pointed out that in this version, each member of the assembly (323) is either insulated from electrical contact with the surrounding blood or is of a more "noble" metal in the electromotive series than is the metallic alloy of the link (321). Insulation of the assembly (323) may be accomplished by coating in some appropriate fashion with an electrically non-conductive polymer such as polytetrafluoroethylene or polyxyxylene. In any event, the passage of a small voltage through the core wire (310) to erode the link and release the cage assembly (302) is easily accomplished using the concepts discussed in U.S. Pat. Nos. 5,122,136 and 5,354,295, both to Guglielmi and Sepetka, and in 5,423,829 to Pham et al. Each of these documents is specifically incorporated by reference. Each of these documents describes such a joint or link in conjunction with the placement of a vaso-occlusive device in a vascular site, but the principles of provoking an electrolysis or electro-oxidation of an erodable joint remain the same for the procedure described herein. It should be apparent that an electrical return path to the power supply is to be provided for the procedure involved with this version to be successful.

Figure 8A:
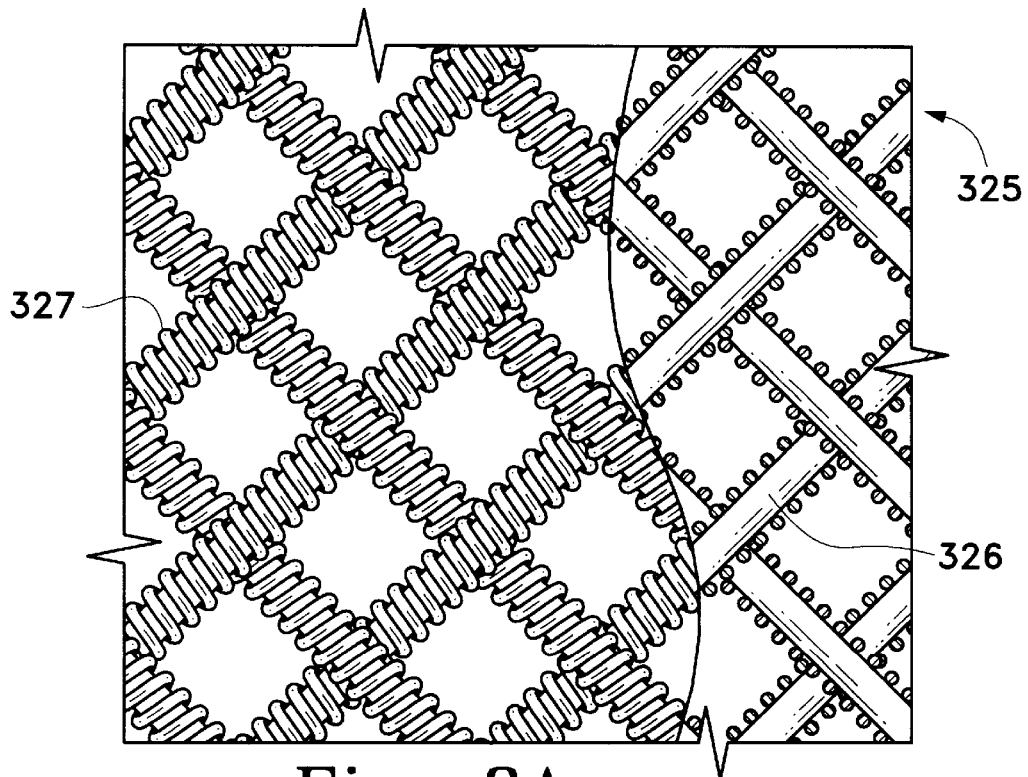
FIG. 8A shows a close-up of braid section comprised of a wrapped wire.
Figure 8B:
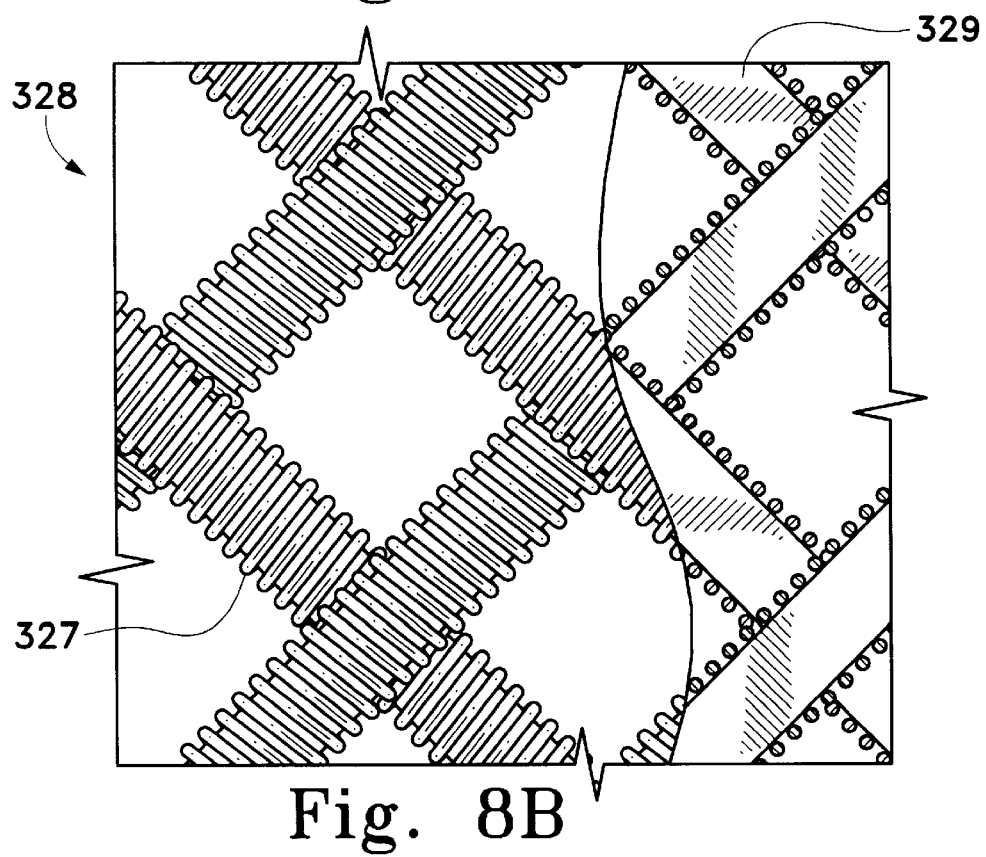
FIG. 8B shows a close-up of braid section comprised of a wrapped ribbon.

As noted elsewhere, the location of the cage assembly should be visible using fluoroscopy. Various methods have been suggested above. One highly preferred method is shown in FIGS. 8A and 8B. In essence, at least some of the elements (ribbons or wires) making up the cage assembly are provided with significant radio-visibility via the placement of a radio-opaque covering on these elements. A metallic coating of a metal having comparatively more visibility, during fluoroscopic use, than stainless steel is preferred. Such metals are well-known but include gold and members of the platinum group of the Periodic Table, e.g., platinum, palladium, rhenium, rhodium, etc. The cage assembly wires or ribbons may be electroplated or otherwise provided with a continuous coating but a thick coating may be had by wrapping the element with a radio-opaque wire or ribbon.

FIG. 8A shows a portion of a cage assembly (325) made up of a woven braid of wires (326) which in turn are tightly wrapped with radio-opaque wires (327). The right side of FIG. 8A is a partial cut away showing the wires (326) below the radio-opaque wires in cross-section (327).

As an example of the device shown in FIG. 8A, we have found that nickel/titanium superelastic alloy wire having a diameter in the range of 0.001" to 0.004" wrapped with 0.001" to 0.002" diameter platinum wire is suitable and is quite visible.

FIG. 8B shows a partial cut away of a cage assembly (328) constructed of ribbon (329) as described above and further wrapped with radio-opaque wires (327). As was the case with the FIG. 3A variation, the right side of the drawing is a partial cut away showing the internal ribbon (329).

The variations of the cage assemblies shown in FIGS. 8A and 8B may be used in place of any of the cage assemblies found elsewhere herein.

Figure 9A:
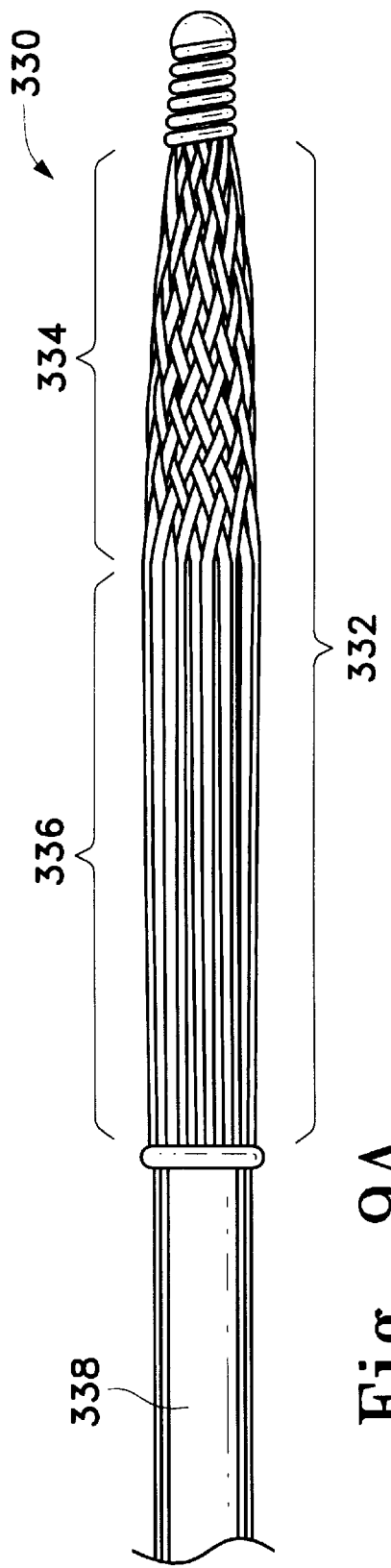
FIGS. 9A and 9B show, respectively, side views of a braided version of the device as expanded and as unexpanded but having an unbraided proximal portion.
Figure 9B:
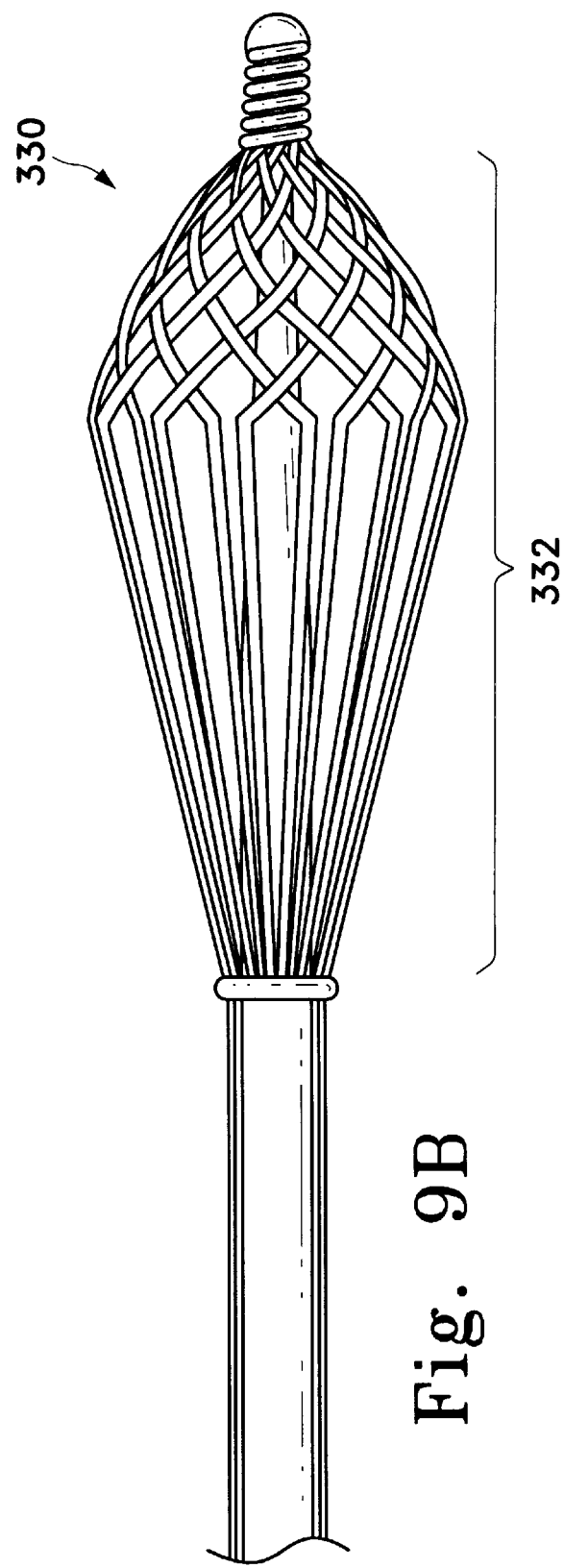

FIGS. 9A and 9B show a further variation (330) of the inventive device utilizing a partially braided cage assembly (332). In this variation, the cage assembly (332) has a distal conical section (334) and a non-woven proximal section (336). Otherwise the variation is the same as is found FIGS. 5A and 5B. The generally linear ribbon components of the proximal section of (336) are more apt to move laterally when encountering an embolic mass and to allow that mass to pass to the tightly woven net distal section (334) for collection. It is within the scope of this invention that the ribbons of the proximal section (336) be twisted ninety degrees so that the narrow edge of the ribbons in this region are generally parallel to the axis of the core wire (338) and consequently provide a minimum surface area to the mass to be removed.

Although not shown in conjunction with the Figures, we alternatively contemplate the use of a cylindrical mid-section such as is found in FIG. 6B as (313) in this variation.

Figure 10A:
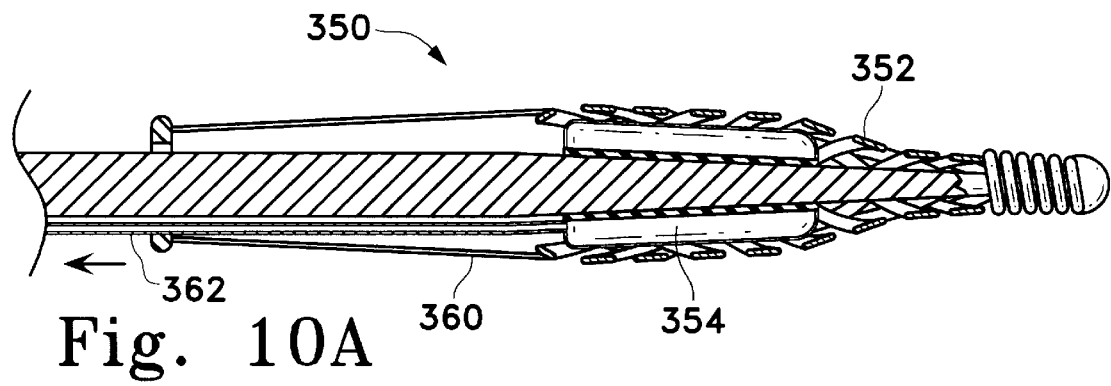
FIGS. 10A, 10B, and 10C show a cut away side-view of the inventive device utilizing a balloon as an expansion actuator.
Figure 10B:
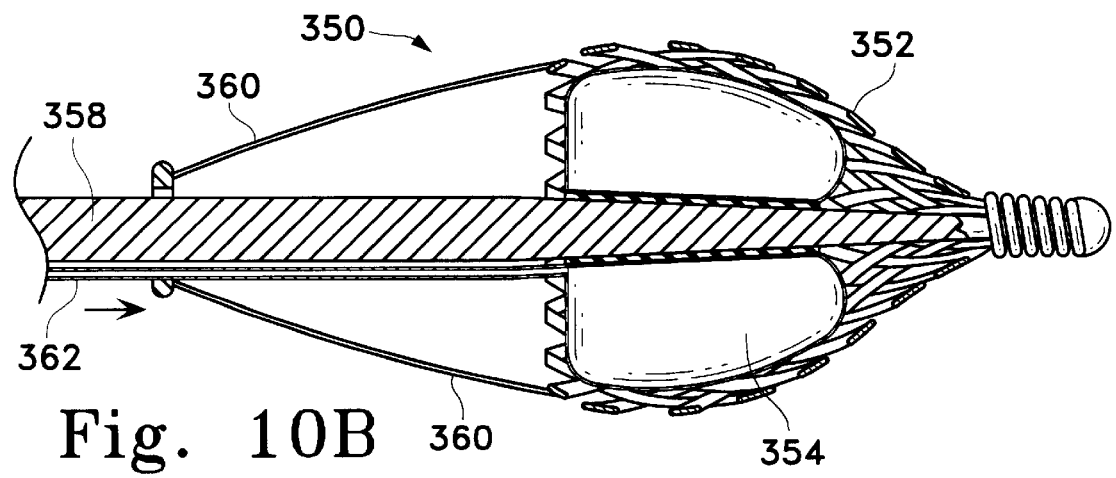
Figure 10C:
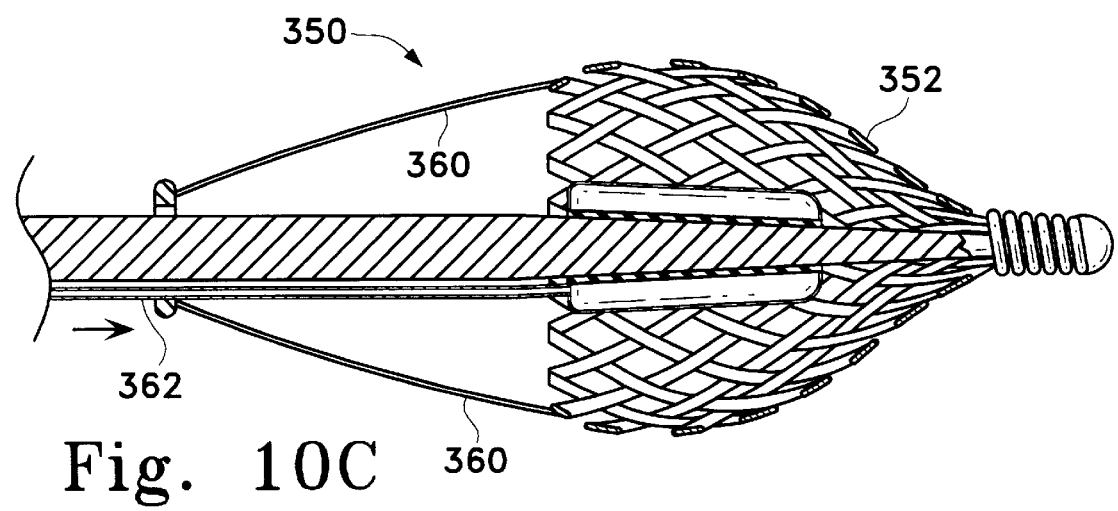

FIGS. 10A, 10B, and 10C show a variation (350) of the inventive device depicting two independent concepts. First, the cage assembly (352) is braided and has no proximal sector. Second, the deployment is aided by the use of an optional micro-balloon (354).

Specifically, cage assembly (352) is a rosebud-shaped braid (as shown in FIG. 10B). It is maintained in a collapsed condition against core wire (358) by a number of actuators (360). The cage assembly (352) is constructed in the same way and using the same materials as those braided cage assembly discussed above. Although the cage assembly (352) is self-expanding, this variation of the invention includes a micro-balloon (354) which is shown inflated in FIG. 10B and deflated in FIG. 10C. The balloon (354) may be used in this way to assist in the expansion of the cage assembly (352). Although not critical to this variation, the balloon may be sized so that it does not extend to the proximal end of the cage assembly (352). In this way the balloon (354) is available to hold the cage assembly (352) in the center of the lumen, maintain a controllable amount of force on the cage assembly (352) radius, and yet maintain room within the proximal end of the cage assembly (352) for the desired embolus collection.

Alternatively to (or in addition to) the balloon (354), actuator elements (360) may also be used to control the expansion of cage assembly (352). An axially movable sheath (362) may be used in conjunction with the actuator elements (360) in the manner discussed above.

The actuator element (360), as well as each of the analogous elements discussed above, may either be very flexible in which case they are used only in tension to hold the cage assembly against the respective core wires or they may be of such a stiffness that they may be used both in tension to maintain the cage assemblies against the core wire and then used in compression to assist in expansion of the cage assembly. In general, the choice of size of the actuator elements is a matter for the designer of a particular variation of this device. The factors entering into such a decision include such diverse matters as the size of the vessel to be recanalized and its tortuousity, the length of the occlusion, and then secondarily, the composition and size of the components woven into the cage assembly.

Figure 11:
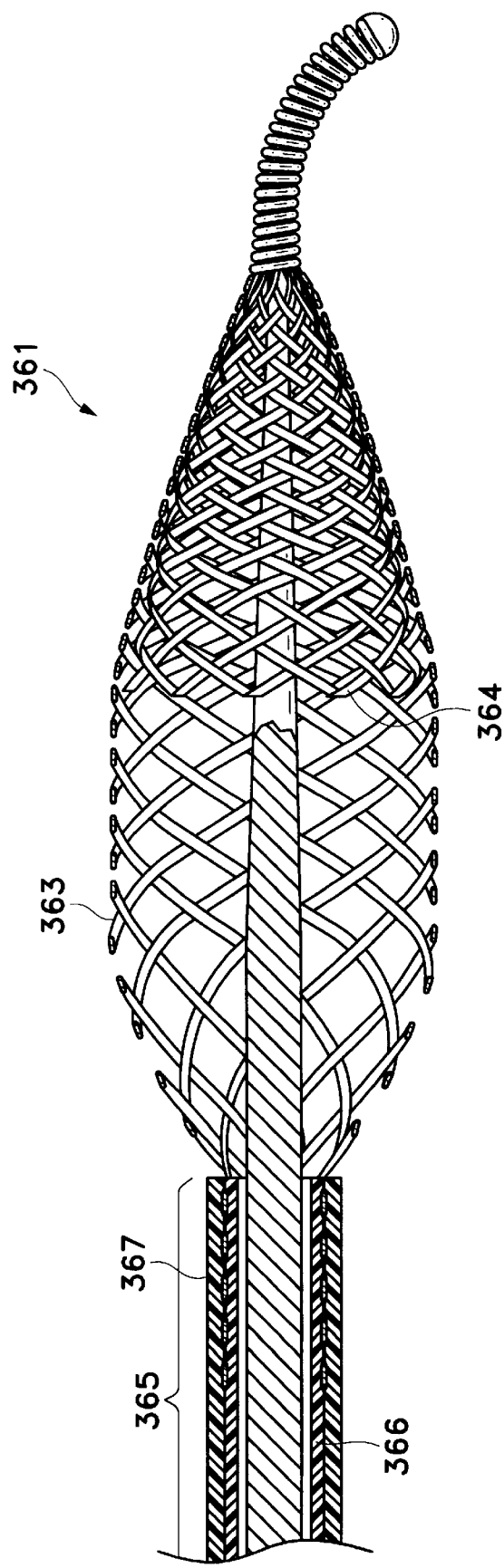
FIG. 11 shows a partial cross section of a variation of this invention using a tubular actuator and a supplemental embolism collector assembly.

FIG. 11 shows in partial cross section a variation (361) of the inventive device. In particular, the figure depicts two concepts which may be independently used in any variation of the invention. Specifically, FIG. 11 shows a structure for augmenting the distal portion of the cage assembly and shows a specific variation of the actuator assembly which eliminates the wires and rods shown in the variations discussed above.

In particular, this variation (361) includes a cage assembly (363) and has located therein in its distal section an inner cage element (364). The inner cage element (364) is depicted as a braided member. However, it need not necessarily be a braid, it may be a non-woven fabric or mere filaments placed in the distal region of the cage assembly (363) to help with the collection of clot material. The inner cage element (364) may be metallic wire or ribbon or a natural or synthetic polymeric fiber or ribbon. It is within the scope of this invention that the interior cage element (364) be tethered to the outer cage element (363) at the proximal end of the inner cage element (364) or may be fixedly attached to the components of the cage assembly (363) in a variety of positions throughout the assembly. It is further within the scope of this variation that the inner cage element (364) comprise a ribbon or fibers molded or otherwise fixedly attached directly to the cage assembly (363).

One criteium for a selection of material in placement of the inner cage assembly (364) is that it must not interfere with the deployment or expansion of the assembly after deployment.

The placement of inner cage element (364) is important only to the extent that it enhance the ability of the overall assembly to collect portions of the clot. Although FIG. 11 shows the inner cage element (364) as extending to the distal end of cage assembly (363), such is not required. If the inner cage element proves to be too thick and causes the more distal portion of the element to become inflexible or ungainly, the most distal portion of the element may be omitted. Indeed we believe that because of the natural tendency of the clot to be self adhering, it may not be necessary to cover the majority of the distal portion of the conical region of the outer cage element (363) with the inner cage element (364) at all. Similarly, because of the inherent consistency of the material to be removed from the arterial site, the proximal end of inner cage element (364) may be situated at a variety of sites within cage assembly (363). However, it is highly unlikely that the leading edge of inner cage element (364) should ever be placed as far proximal as the region having decreased braid spacing or decreased radius as the cage assembly (363) begins to approach actuator element (365).

As noted above, the inner cage element (364) may be used with any variation of the invention described herein. Further, tubular actuator assembly (365) may be used with any variation of the invention shown herein. This variation depicts a multi-layer tubular assembly as the actuator assembly (365). In particular, the inner tubing member (366) is desirably, but not necessarily, made of lubricious material such as polytetrafluoroethylene. Such a material often increases the ease with which the collector assembly (363) may be expanded after deployment. It is not necessary, however. The inner layer (366) may be omitted if so desired or replaced with other less lubricious materials such as polyurethane, polypropylene, polyethylene, and materials widely known and used in this industry. Similarly, the outer tubing member (367) should suitably be of a material which is compatible with and adherable to the inner tubing member. That is to say that outer tubing member (367) may be a material such as polyurethane or polyethylene or polyvinylchloride. When polytetrafluoroethylene (e.g., Teflon) is used as the inner member (366) and polyurethane is used in the outer layer (367), it is often desirable to etch the outer surface of tubing (366) using known etching techniques to provide a surface suitable for joining to the outer polyurethane layer (367). Further it is often desirable to use a biocompatible epoxy such as TRA-CON TRA-BOND FDA-2 (Tra-Con, Inc.—Medford, Mass.) as the material which provides adherence between the outer tubular member (367) and the inner tubular member (366). Typically, such adhesive is necessary or desirable only in the region in which the proximal end of collection element (363) extends proximally into the region between the two polymeric layers.

The core element and distal coil in this variation are as discussed elsewhere.

Figure 12:
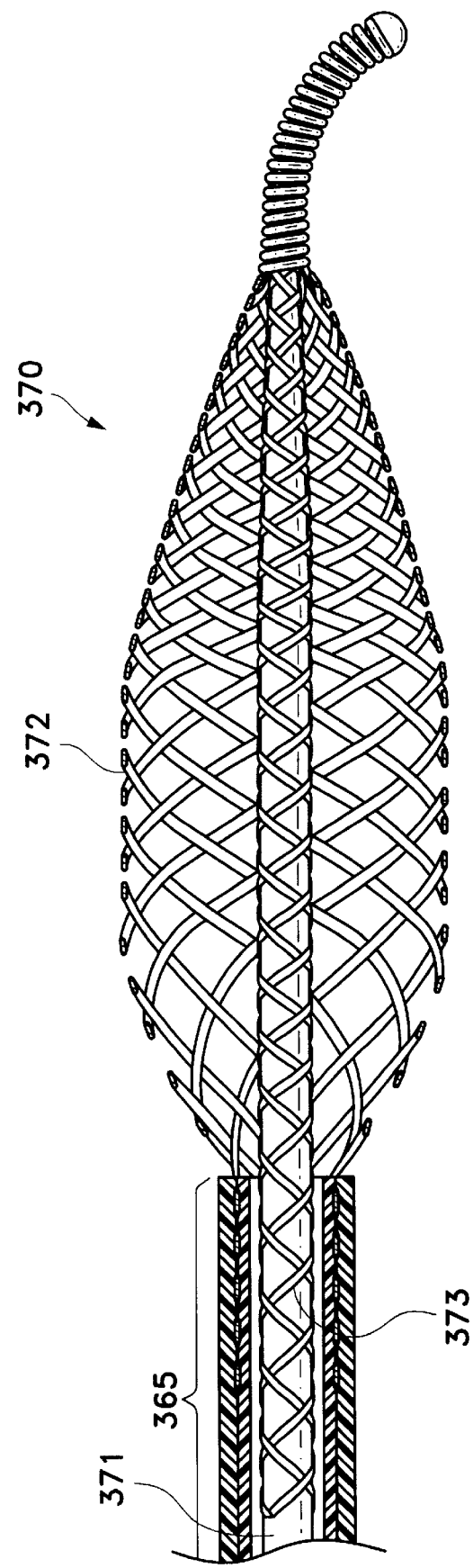
FIG. 12 shows a variation of the invention in partial cross section utilizing a braid enhanced core assembly wire.

FIG. 12 shows a highly desirable variation (370) of this invention. It utilizes a core assembly made up of a core wire (371) and a braid member (373) which is adherent to the outer surface of core wire (371). We have found that when designing embolectomy devices such as these for use in tortuous vasculature, it is difficult to maintain the outer tubular or actuator portion (365) in tension against the compression of core assembly (371) without some amount of bending or helical twisting in the region of the embolism collector assembly. This twisting is obviously undesirable when placing the device in the vasculature in that it simply makes the placement that much more difficult. We have found that by placement of braid (373) upon core wire (371), the resulting assembly has significant column and torsional strength particularly when compared to the interior wire alone. The placement of this highly preferred braid (373) is desirably at least from the distal end of cage assembly (372) to the proximal end of the element (372) during the step of placement at the treatment site. Desirably (and as shown in FIG. 11), the braid element (373) may extend at least for some distance within the lumen of actuator assembly (365). And indeed, the whole or any part of core wire (371) may have braid element (373) placed thereon.

We have found that braid (373) is desirably of a super-elastic alloy such as makes up the braid of the cage assembly (372). This is not absolutely necessary, but, again it is highly desirable. All or a portion of the elements making up braid element (373) may be super-elastic alloys, stainless steels, radio-opaque materials such as platinum, and even organic and inorganic fibers or ribbons such as KEVLAR and carbon fiber.

As is the case with the other variations of the invention, the use of braid enhanced core assembly, although highly preferred, is optional but suitable for use with each of the variations.

FIG. 13 shows still another variation (380) of the inventive device. This Figure shows the presence of a braid (382) within the actuator element. The actuator element is shown in a partial cross section and is made up of an inner tubing member (383), the braid member (382), and an outer tubing member (384). This variation provides for significant kink resistance and torsional stiffness to the actuator assembly. This is an effective structure for minimizing the diameter of the actuator assembly and yet providing it with sufficient strength and flexibility to undertake the task of accessing clots in very distal and tortuous portions of the vasculature.

In the variation shown in FIG. 13, the proximal portion of cage assembly (372) is placed between the outer layer (384) and the inner layer (383). As was the case with the variations discussed above, that portion may also be glued in place but may be simply squeezed between the two polymeric layers for good results. It is also within the scope of the invention to place the proximal portion of the clot cage assembly (372) on the exterior or on the interior of a single layer of polymer and suitably adhere that portion of the clot collector element to the tubular member.

FIG. 14 shows still another variation (386) of the inventive device. In this variation, the core element comprises tubular member (387) which is fixedly attached distally to the cage assembly (372) and the core wire (388) is movable and removable from the lumen of tubular element (387). With this device, the attending physician is able not only to address the clot with the device as has been discussed above and is discussed in more detail below, but is also able concurrently to introduce clot dissolving medications such as urokinase through the lumen of inner tubular member (387) during, before or after the clot is in the process of being removed. Also shown in FIG. 14 are a number of orifices (389) located proximally of cage assembly (372) through which fluids such as the listed thrombolytics may pass. These orifices (389) may be used on any variation disclosed herein. Of course, the core wire (388) is typically removed so to allow maximum flow of the desired medication. Some flow is possible in the annulus between core wire (388) and inner tubing member (387) but it is much more desirable to remove the core wire (388) prior to introducing the liquid treatment material into the inner tubular member (387) lumen. Because of the size of the devices made for use in the vasculature of the brain, it is likely that a product designer would choose a braided member as the constituent of inner tubing member (387). Coil supported tubular members such as those described in U.S. Pat. No. 5,454,795 and our U.S. patent application No. 08/338,018, filed Nov. 10, 1994, entitled "High Performance Spiral Wound Catheter" are also excellent choices for this variation of the device. These braid or coil enhanced tubular members provide sufficient strength for the overall device (386) so that, when stretched, the device does not bend or gather a helical twist because of the inherent stresses placed on portions of the device during introduction into the clot area.

FIG. 15A shows a desirable variation (390) of the inventive device. We have observed that with a number of the other variations of this invention, when the core wire is fixedly attached to the distal end of the cage assembly, the ability to use the core wire as a guidewire is somewhat inhibited. That is to the say that in the instances where the core wire or element is twisted with respect to the embolism cage assembly, the embolism collector element sometimes loses its structural integrity and becomes difficult to straighten out. It is feasible to produce an actuator which is small enough so that the actuator (along with the core wire or element) may be used to function as a guidewire. However, a truly independent guidewire is often desirable. This variation (390) of the invention frees the core wire (391) to function as a guidewire without substantial fear of destroying the shape integrity of the embolism cage assembly (392). In this variation, core wire (391) is rotatably attached to embolism cage assembly (392). The core wire (391) rotates within distal collar (393). Distal collar (393) is fixedly attached to cage assembly (392). Distal of the cage assembly (392) may be found a radio-opaque coil (394) fixedly attached to core wire (391). The outer diameter of radio-opaque coil (394) is larger than the inner diameter of collar element (393) and so does not pass through the interior. Retainer element (395) is also fixedly attached to core wire (391). Retainer element (395) limits the longitudinal or axial movement of the core wire (391) within a small distance through collar (393). Retainer element (395) is central to the function of maintaining the cage assembly (392) in a collapsed or first deployment shape during the time the device (390) is being deployed. The remainder of the elements seen in FIG. 15A such as the actuator assembly (396) and the distal tip (397) of the device are all of the same configuration as shown in the various other variations of the invention. It should also be noted that the core wire in this variation is preferably adherent to a braid (401) such as was discussed above with regard to FIGS. 7A, 7B, and 7C.

This variation (390) is used in the same way as is the variation shown in FIG. 14 except that the guidewire is not extensile from the distal end of the device, but it has the advantage of being potentially thinner than that device.

FIG. 15B shows another most desirable variation (399) of the inventive embolectomy device. This variation is quite similar to that described in FIG. 14A in that it utilizes a rotatable core wire (391) with an adherent braid (401). It also has a retainer element (395) which is shown to be in the form of a few turns of a radio-opaque coil. Added to this variation (399) are two independent concepts. The first, and most important of the two, is the use of an anti-deployment spring (403). It is placed on the exterior of the braided core wire (391) and, as the device (399) is deployed, the spring is in slight compression between the distal end of the actuator and the distal end of the embolism cage assembly (392). It tends to hold the cage assembly (392) tight against the core wire (391). It should be understood, of course, that this device is intended to provide a very small profile for passage of the device through or by a clot. Use of the spring (403) provides such a low profile without further manipulation by the user outside the body. In this variation, the actuator is used to compress the spring (403) and deploy the cage assembly (392).

Although the remainder of the device (399) is quite similar to the variation (390) shown in FIG. 15A, the second difference is the use of a friction reducing coil (405). The diameter of the coil wire used in this variation is quite small, e.g., often less than 1 mm in diameter. This feature is only an improvement, it is not a necessary portion of the invention.

Further, one might observe from FIG. 15B that the independent collar (393) found in FIG. 15A is eliminated. In this variation, the reduced diameter distal throat for the device (392) is instead made of the distal end of anti-deployment spring (403) and the distal end of the braid making up embolism collection device (392). The two components are simply held in place and a thermoplastic is melted into their junction. A material such as thermoplastic polyethylene with a small amount of EVA functions well in this service. Other obvious joining techniques and materials are also suitable, e.g., gluing, welding, soldering, etc.

In any event, the core wire operates in precisely the same way as does the core/guidewire found in the variation of FIG. 15A. It should be observed that although the variations shown in FIGS. 15A and 15B show the distal marker coil (394) as being closely adjacent the distal or collar region of the cage assembly (392), such is not necessarily the case. One may produce the device with a core wire which does not move longitudinally with relation to the distal end of the cage assembly (392) or in certain circumstances it may be desirable to allow the core wire a significant but limited amount of longitudinal movement before the core wire reaches the point where it is able to cause the cage assembly (392) to increase its diameter and deploy. Said another way: the core wire (391) may move longitudinally within the distal end of the cage assembly (392) but may not be removed from within the distal end of the cage assembly (392).

Figure 16:
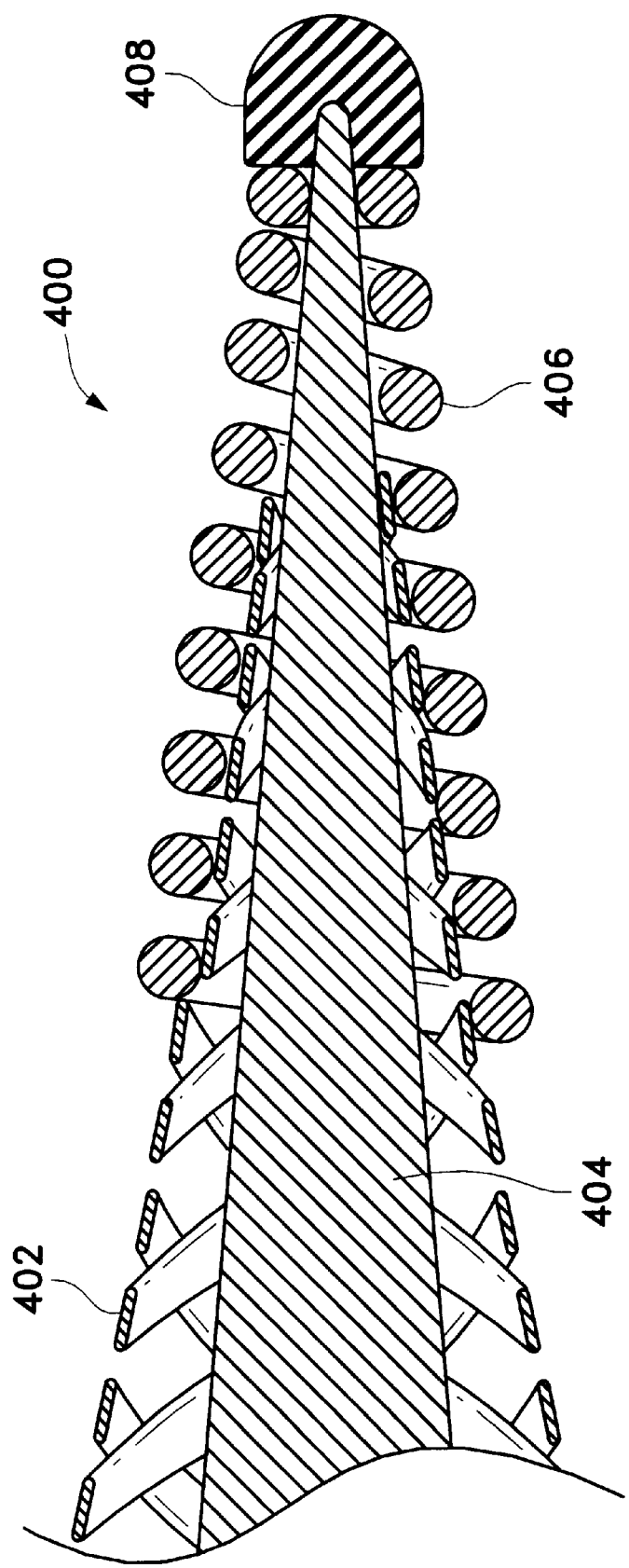
FIG. 16 is a close up partial cut away of a distal tip of the inventive device showing a desired way of fixedly attaching the cage element to the core wire.

FIG. 16 shows a detail of the most distal tip of the device and in particular depicts a desirable way to fixedly attach the cage assembly to the core wire.

The distal assembly (400) utilizes a cage assembly (402) which at its most distal region is held against the core wire (404) by a (desirably) radio-opaque coil (406). An atraumatic tip (408) may be placed on the tip of the core wire (404). The tip (408) is typically of the same material as is the coil (406). These various pieces of metal (core wire (404), coil (400), and cage assembly (402)) may be soldered together although other metal joining techniques such as brazing or welding may be used. A flux is used for soldering or brazing and must be chosen with care to achieve the desired joint amongst the various differing metals and alloys.

Figure 18A:
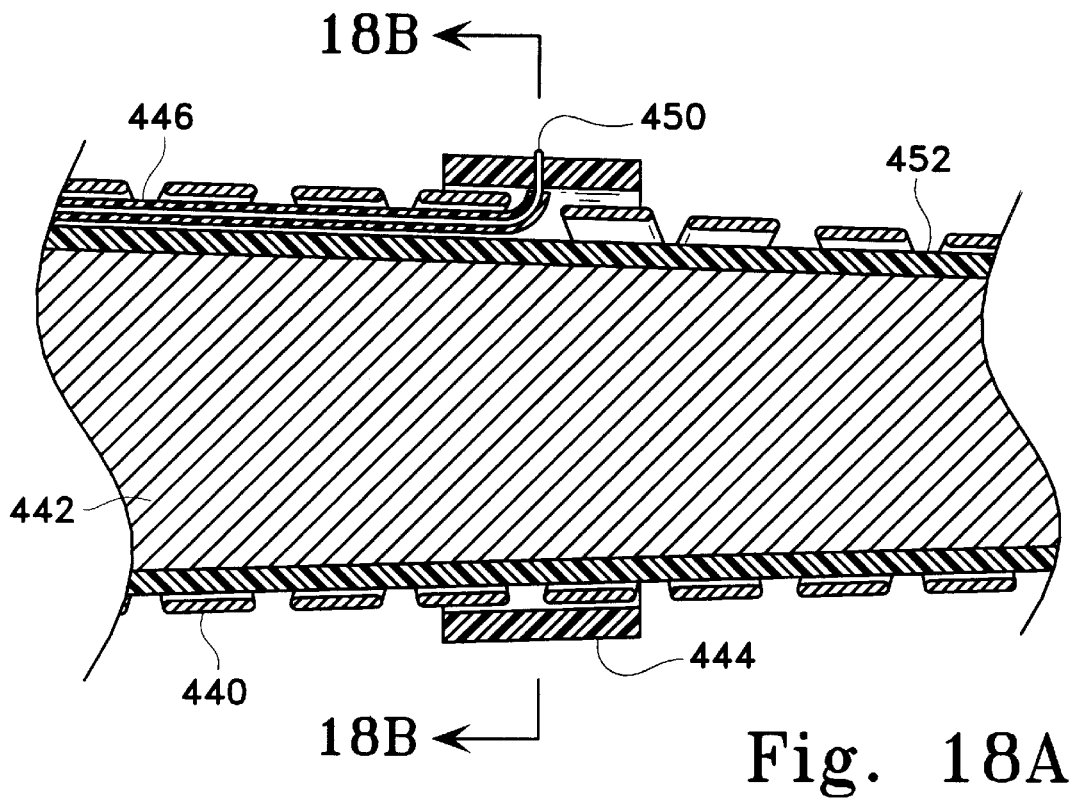
FIGS. 18A and 18B show partial, cut away, side view and cross sectional end views of the release mechanism shown in FIGS. 17A and 17B.
Figure 18B:
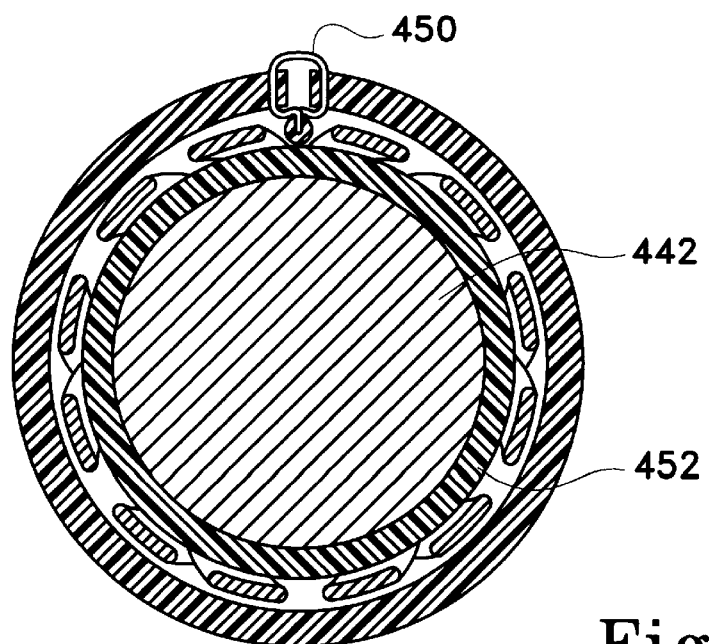

FIGS. 17A and 17B show another variation of the invention using electrically erodable or electrolytically erodable bands to loose the self-expandable cage assembly in place of the actuator elements or balloons. FIGS. 18A and 18B show details of one such erodable linkage.

FIG. 17A shows a braided cage assembly (440) held in tight compression against the core wire (442) by a pair of bands (444) having an electrically erodable link therein. Upon severing the link (shown as (444) by example in FIGS. 17A and 17B), the bands (444) open and the braided cage assembly (440) expands as shown in FIG. 17B. This version has a number of benefits over the mechanical and hydraulic variations discussed earlier. First, the cage assembly (440) may be made of material having substantially more springiness than normally suitable for use when using mechanical releases. This is so because the mechanical release actuators have very little mechanical advantage in pulling the cage assembly down to the core wire since they run parallel to that core wire. Since the stress applied to the actuators must be offset by one in the core wire, the core wire must be made larger or of stiffer material to counteract the applied stress. The various tensions also make the assembly somewhat stiffer and therefore more difficult to manipulate in tortuous passageways.

In contrast, the bound variations shown in FIGS. 17A, 17B, 18A, and 18B need not have the same axial mechanical strength to carry the axial stresses of the actuators. The core wire may then be made smaller and more flexible (if such flexibility is desired), and the cage assembly may be given more springiness than would be available in the mechanical release form.

The detriment is that each of the elements in the assembly must be insulated from electrical contact with the bloodstream or constructed of materials which are more "noble" in the electromotive series than the material making up the erodable link. Insulating such components with coatings of PARALENE or polyfluorocarbon polymers is time-consuming and expensive.

Electrolytic separation occurs after a small current is applied to insulated conductor (446) which is an electrical connection with the metallic sacrificial link (not shown in FIGS. 17A and 17B). The voltage passes through the sacrificial link into the surrounding blood and other fluids and completes the circuit through the body via an electrode placed, e.g., in or on the delivery catheter.

Two bands (444) are shown in the drawings; more may be desirable or only one may be needed. The number and design of the bands is a matter of detail for the device designer.

One desirable design for the release bands (444) is shown in FIGS. 18A and 18B. The band (444) is depicted as a split polymeric ring held tightly in place around the cage assembly (440) by a sacrificial link (450). The sacrificial link is, e.g., stainless steel wire of a diameter of about 0.001 inches and is electrically attached to an insulated power supply wire (446). The insulating covering (452) placed on the exterior of the core wire (442) may be seen in the Figures. It is within the scope of this invention that the distal coil tip be used as the return electrode completing the electrical circuit through the center of the core wire to the not seen power supply. Erosion of the sacrificial link allows the ring to open and the cage assembly to deploy.

FIGS. 19A to 19E depict the generic procedural steps for the use of the inventive device.

Figure 19A:
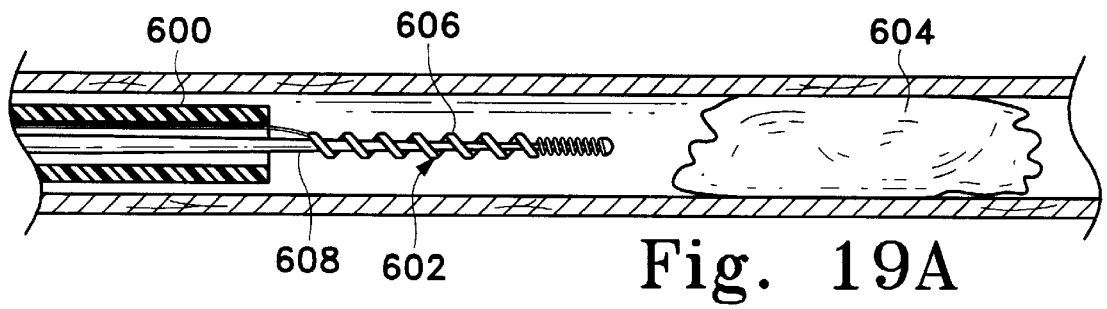
FIGS. 19A, 19B, 19C, 19D, and 19E show a generalized sequence of steps for use of the inventive device to remove an embolism.

In FIG. 19A, a catheter (600) is used to place the inventive device (608) just proximal of the embolism (604) to be removed. In this procedure, the inventive device is used as an embolectomy device. The cage assembly (606) is held against the core wire (608).

Figure 19B:
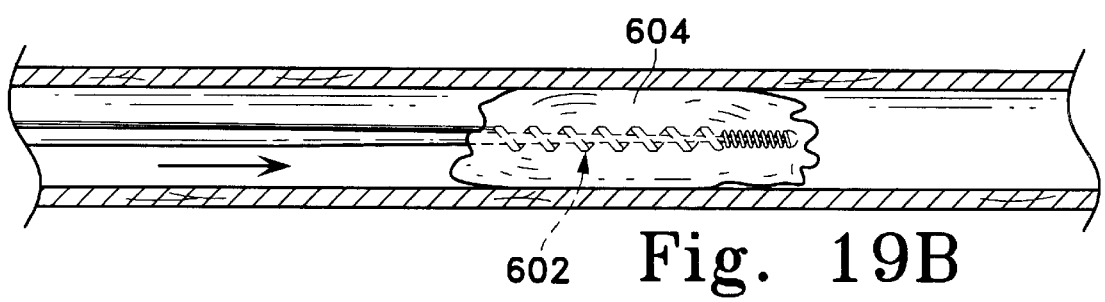
Figure 19C:
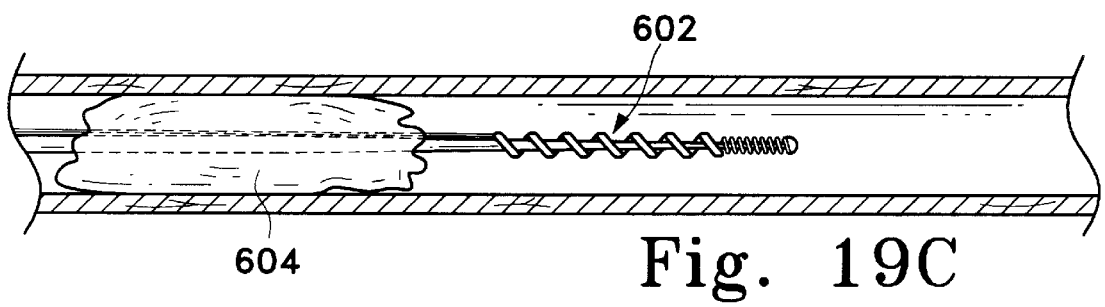

FIG. 19B shows the penetration of the occlusion (604) by the embolectomy device (602) and FIG. 19C shows the embolectomy device emerging from the distal end of the occlusion (604).

Figure 19D:
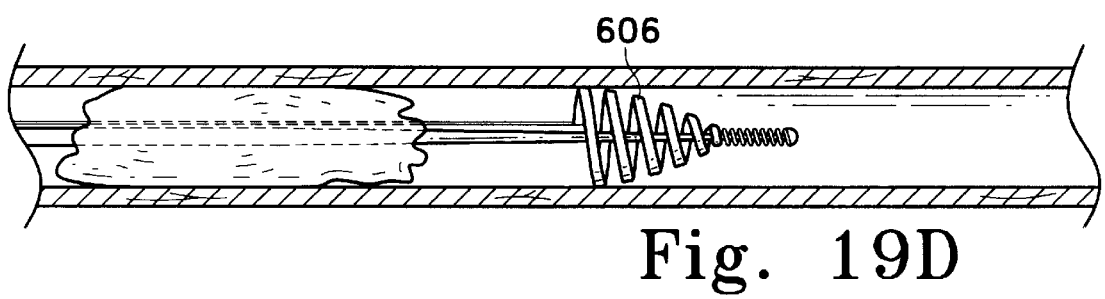

FIG. 19D shows a cage assembly (606) after completion of its self-expansion.

Figure 19E:
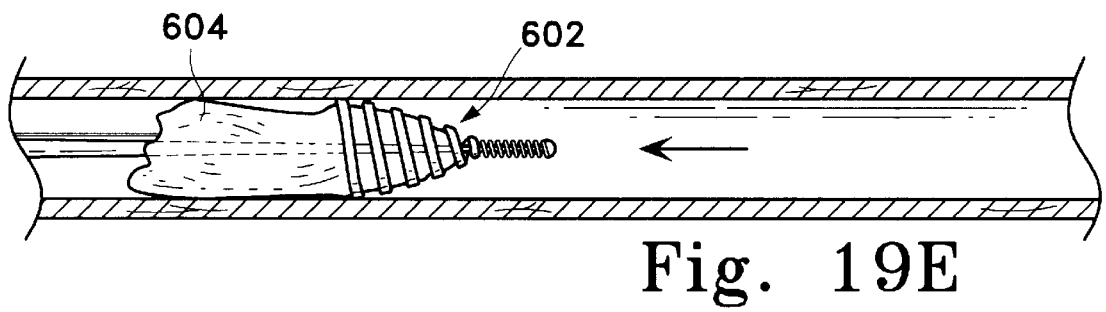

FIG. 19E shows the embolism removing device (602) being moved proximally to remove the embolism (604).

FIGS. 20A–20D show a procedure for bypassing a clot using the inventive device.

Figure 20A:
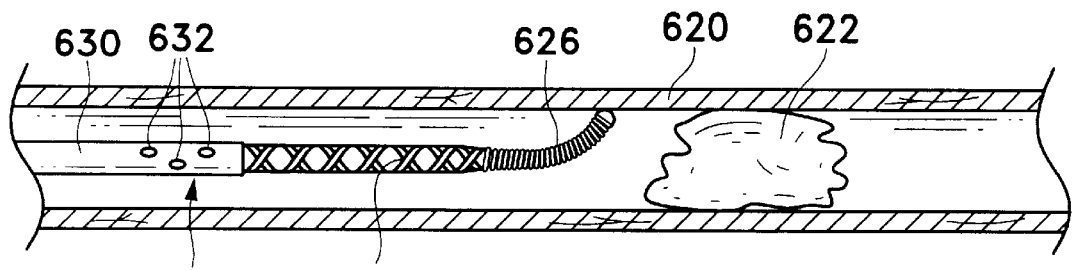
FIGS. 20A–20D show a generalized sequence of steps for displacing a thrombus for restoration of flow past the occluded site.
Figure 20B:
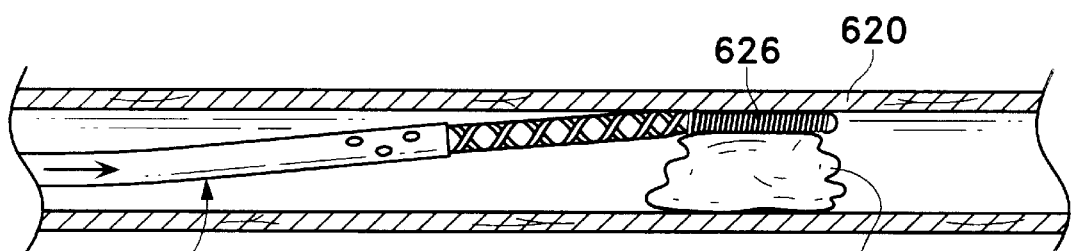

FIG. 20A schematically depicts an artery (620) containing a blocking clot (622). A variation of the inventive device (624) similar to that shown in FIG. 14 is shown in the artery (620). This variation (624) has a rotatable core wire (626) which is useful as a guidewire. It has a woven braided cage assembly (628) and a tubular actuator (630) with orifices (632) for perfusion of appropriate medicines.

Many clots such as that found at (622) will push the guidewire (626) aside as it contacts the clot. Indeed, in most instances, such is preferred. The corewire (626) then slips along the wall of the artery (620) as the device (624) is advanced.

Figure 20C:
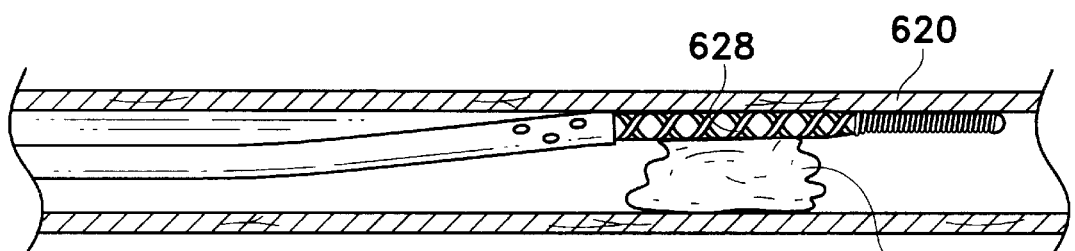
Figure 20D:
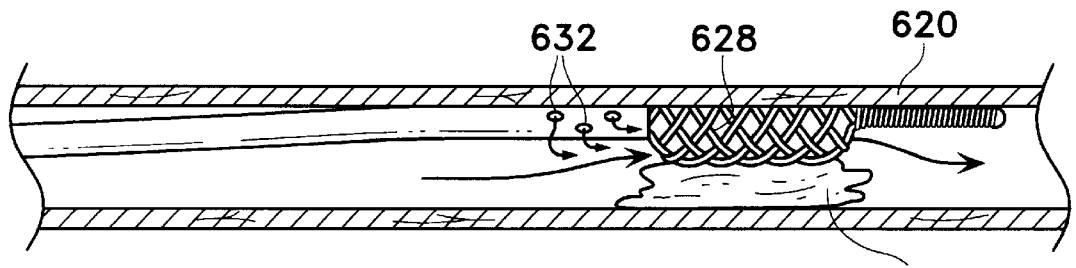

FIG. 20C shows an appropriate placement of the cage assembly (628) prior to deployment. The cage assembly (628) is selected so that it overlaps both ends of clot (622).

Upon deployment of cage assembly (628) to its expanded shape, blood will flow from the arterial to venous end of the clot (622) through the lumen of the open cage assembly (628). Thrombolytics may be introduced through the orifices (632) to dissolve clot (622). It is highly desirable that the cage assembly (628) be used to restrain the clot (622) from movement in the vessel so that the thrombolytics may completely dissolve the clot (622) while so restrained. This procedure obviously provides a continuing source of thrombolytics to the clot (622) and further provides a large clot surface area upon which the thrombolytics may work. Of course, the cage assembly (628) may also be used as in the procedure of FIGS. 19A–19E if so desired.

It should be apparent that the cage assembly of this invention may be re-collapsed and re-deployed as necessary to displace or collect emboli as necessary or desired.

A final note on the construction of the devices: it is obviously valuable to be able to ascertain the outline of the cage assumably discussed above both before and after deployment. Consequently, the use of radio-opaque markers is very valuable. The design and of such is routine and is within the skill of an ordinary designer in this art. Similarly, obvious variants of the invention described above are within the scope of the invention. This and other known or non-critical items have been omitted from the drawings for the sake of brevity and clarity of the invention disclosed here.

We claim as our invention:

1. An embolism treatment device comprising a core element and a cage assembly:
    a. said core element having a distal end and a proximal end and comprising at least a rotatable core wire adapted to pass through, to be rotatable with respect to, and to be non-removable from said cage assembly, and
    b. said cage assembly having a distal end and a proximal end, and comprising a super-elastic alloy braid substantially coaxial to said core element, said cage assembly coaxial to said core element and having a first deployment shape and a second larger expanded shape, said second larger expanded shape being different from the first deployment shape, and said cage assembly distal end being rotatably attached to said rotatable core wire.

2. The embolism treatment device of claim 1 wherein said first deployment shape is coaxially adjacent said core element.

3. The embolism treatment device of claim 1 further comprising an actuator element connected proximally to said cage assembly and wherein said cage assembly has a first deployment shape adjacent said core element when said actuator element is in a first deployment position and said second expanded shape when said actuator element is in a second deployment position.

4. The embolism treatment device of claim 1 wherein the cage assembly second expanded shape comprises a cylindrical section between said distal end and said proximal end.

5. The embolism treatment device of claim 1 wherein said cage assembly is radio-opaque under fluoroscopy.

6. The embolism treatment device of claim 5 wherein said superelastic alloy braid is comprised of a member selected from the group consisting of wires and ribbons covered by a radio-opaque covering.

7. The embolism treatment device of claim 6 wherein the radio-opaque covering comprises radio-opaque wire wrapped around said braid members.

8. The embolism treatment device of claim 1 wherein the braid is relatively more tightly woven distally.

9. The embolism treatment device of claim 8 wherein the braid is relatively less tightly wound proximally.

10. The embolism treatment device of claim 1 wherein the cage assembly is braided proximally.

11. The embolism treatment device of claim 1 wherein the cage assembly is not braided proximally.

12. The embolism treatment device of claim 1 wherein the cage assembly is self deploying.

13. The embolism treatment device of claim 1 wherein the cage assembly has a decreasing radius distally.

14. The embolism treatment device of claim 1 wherein the core element further comprises a helically wound radio-opaque coil fixedly attached to said rotatable core wire distally of the cage element.

15. The embolism treatment device of claim 1 wherein the cage assembly comprises a nickel-titanium alloy.

16. The embolism treatment device of claim 1 wherein the cage assembly comprises a minor number of ribbons comprised of radio-opaque alloys.

17. The embolism treatment device of claim 2 wherein the actuator comprises a tubular member fixedly attached to the cage assembly.

18. The embolism treatment device of claim 17 wherein said tubular member further comprises a braid.

19. The embolism treatment device of claim 18 wherein said tubular element braid comprises a super-elastic alloy.

20. The embolism treatment device of claim 17 wherein said tubular member further has an inner lumen and an outer surface and has at least one fluid flow orifice from said inner lumen to said outer surface.

21. An embolism treatment device comprising:
    (a) a core wire element having a distal end and a proximal end and a longitudinal axis;
    (b) a cage assembly comprising at least one spirally wound, metallic member having a distal end and a proximal end, wherein said cage assembly is generally coaxial to said core wire element and wherein said distal end of said cage assembly is fixedly attached to said core wire element;
    (c) an actuator fixedly attached to said proximal end of said spirally wound metallic member; and
    (d) a radiopaque tip fixedly attached to said core wire element distally of said cage assembly,
    wherein said cage assembly has a first deployment shape when said actuator is in a first deployment position and a second larger expanded shape different from the first deployment shape when said actuator is in a second deployment position.

22. The embolism treatment device of claim 21 wherein said cage assembly is fixedly attached to said core element distally.

23. The embolism treatment device of claim 21 wherein said first deployment shape is adjacent said core wire element.

24. The embolism treatment device of claim 21 wherein said second expanded shape comprises a trailing conical collector section.

25. The embolism treatment device of claim 21 wherein the cage assembly further comprises a cylindrical section proximally of said distal end.

26. The embolism treatment device of claim 21 wherein the cage assembly comprises at least two spirally wound superelastic alloy members selected from the group consisting of ribbons and wires, said members being wound respectively clockwise and counter-clockwise about the axis of the core wire element.

27. The embolism treatment device of claim 21 wherein the cage assembly comprises a plurality of ribbons woven into a braid.

28. The embolism treatment device of claim 21 wherein the cage assembly is self deploying.

29. The embolism treatment device of claim 21 wherein the cage assembly comprises a nickel-titanium alloy.

30. The embolism treatment device of claim 21 wherein the cage assembly is contained in a first deployment shape by an electrolytically severable band.

31. The embolism treatment device of claim 30 wherein the actuator comprises a tubular member fixedly attached to the cage assembly.

32. The embolism treatment device of claim 21 wherein the core element further comprises a spring element adapted to deploy said cage assembly to said second shape.

33. The embolism treatment device of claim 21 wherein said cage assembly is radio-opaque under fluoroscopy.

34. The embolism treatment device of claim 21 wherein said spirally wound metallic member is selected from the group consisting of wires and ribbons covered by a radio-opaque covering.

35. The embolism treatment device of claim 34 wherein the radio-opaque covering comprises radio-opaque wire wrapped around said spirally wound metallic member.

* * * * *